U S010215202B2

United States Patent
Stewart

(10) Patent No.: US 10,215,202 B2
(45) Date of Patent: Feb. 26, 2019

(54) FLUID-OPERATED APPARATUS, METHOD, AND CIRCUIT

(71) Applicant: Neil Gordon Stewart, Victoria (CA)

(72) Inventor: Neil Gordon Stewart, Victoria (CA)

( * ) Notice: Subject to any disclaimer, the term of this patent is extended or adjusted under 35 U.S.C. 154(b) by 121 days.

(21) Appl. No.: 15/496,738

(22) Filed: Apr. 25, 2017

(65) Prior Publication Data

US 2017/0314585 A1  Nov. 2, 2017

Related U.S. Application Data

(60) Provisional application No. 62/328,116, filed on Apr. 27, 2016.

(51) Int. Cl.
| | |
|---|---|
| *F15B 21/08* | (2006.01) |
| *F15B 15/14* | (2006.01) |
| *F15B 11/10* | (2006.01) |
| *A61C 3/02* | (2006.01) |
| *A61C 1/00* | (2006.01) |

(52) U.S. Cl.
CPC ............ *F15B 21/08* (2013.01); *A61C 1/0038* (2013.01); *A61C 3/02* (2013.01); *F15B 11/10* (2013.01); *F15B 15/149* (2013.01); *F15B 15/1476* (2013.01); *F15B 2211/6654* (2013.01); *F15B 2211/7053* (2013.01)

(58) Field of Classification Search
CPC ..... A61C 1/0038; A61C 3/02; Y10S 415/904; F15B 11/10
See application file for complete search history.

(56) References Cited

U.S. PATENT DOCUMENTS

| 2,984,008 | A | | 5/1961 | Weisberg | 433/27 |
|---|---|---|---|---|---|
| 3,568,318 | A | | 3/1971 | Martin | 433/100 |
| 3,732,934 | A | * | 5/1973 | Brandenberg | B25B 23/1453 173/177 |
| 3,850,078 | A | * | 11/1974 | Polizzi | F01L 31/00 137/624.14 |
| 3,865,505 | A | | 2/1975 | Flatland | 415/49 |
| 4,114,275 | A | * | 9/1978 | Jones | A61C 1/0023 433/101 |
| 4,302,185 | A | | 11/1981 | Hall | 433/27 |
| 4,421,292 | A | * | 12/1983 | Matsui | F16K 31/124 251/60 |
| 4,494,933 | A | * | 1/1985 | Matsui | A61C 1/057 415/904 |

(Continued)

*Primary Examiner* — Thomas E Lazo
(74) *Attorney, Agent, or Firm* — Teitelbaum Bouevitch & McLachlen; Neil Teitelbaum

(57) ABSTRACT

An apparatus for seamlessly activating an on-demand function related to a fluid-driven instrument connects to an output of control valve regulating system pressure during normal operation of the instrument. The apparatus includes a fluid-operated bistable circuit that is switchable from a standby mode to an actuating mode by a brief drop in system pressure. In the actuating mode the circuit acts on a switch or valve to activate the function. Turning off system pressure to a longer time returns the circuit to its standby mode. The circuit includes a two-port biased actuator responsive to pressure imbalance between its ports, which are separately pressurizable through, respectively, an actuator-controlled valve and a flow control module.

18 Claims, 12 Drawing Sheets

(56) References Cited

U.S. PATENT DOCUMENTS

| | | | | |
|---|---|---|---|---|
| 4,635,897 | A | * | 1/1987 | Gallant .................... F16K 7/06 137/375 |
| 4,744,752 | A | * | 5/1988 | Nakayama ........... A61C 1/0038 433/100 |
| 5,567,154 | A | | 10/1996 | Wohlgemuth ................ 433/132 |
| 5,947,729 | A | | 9/1999 | Bell ................................ 433/98 |
| 6,056,260 | A | | 5/2000 | Stewart et al. ................... 251/7 |
| 6,484,959 | B1 | | 11/2002 | Grammenz ................ 242/388.9 |
| 7,435,085 | B2 | | 10/2008 | Gugel et al. ..................... 433/84 |
| 8,777,614 | B2 | | 7/2014 | Brennan et al. ................ 433/98 |
| 9,463,077 | B2 | | 10/2016 | Zolhayat |
| 2013/0189919 | A1 | * | 7/2013 | Haegele .............. A61C 1/0038 454/256 |

* cited by examiner

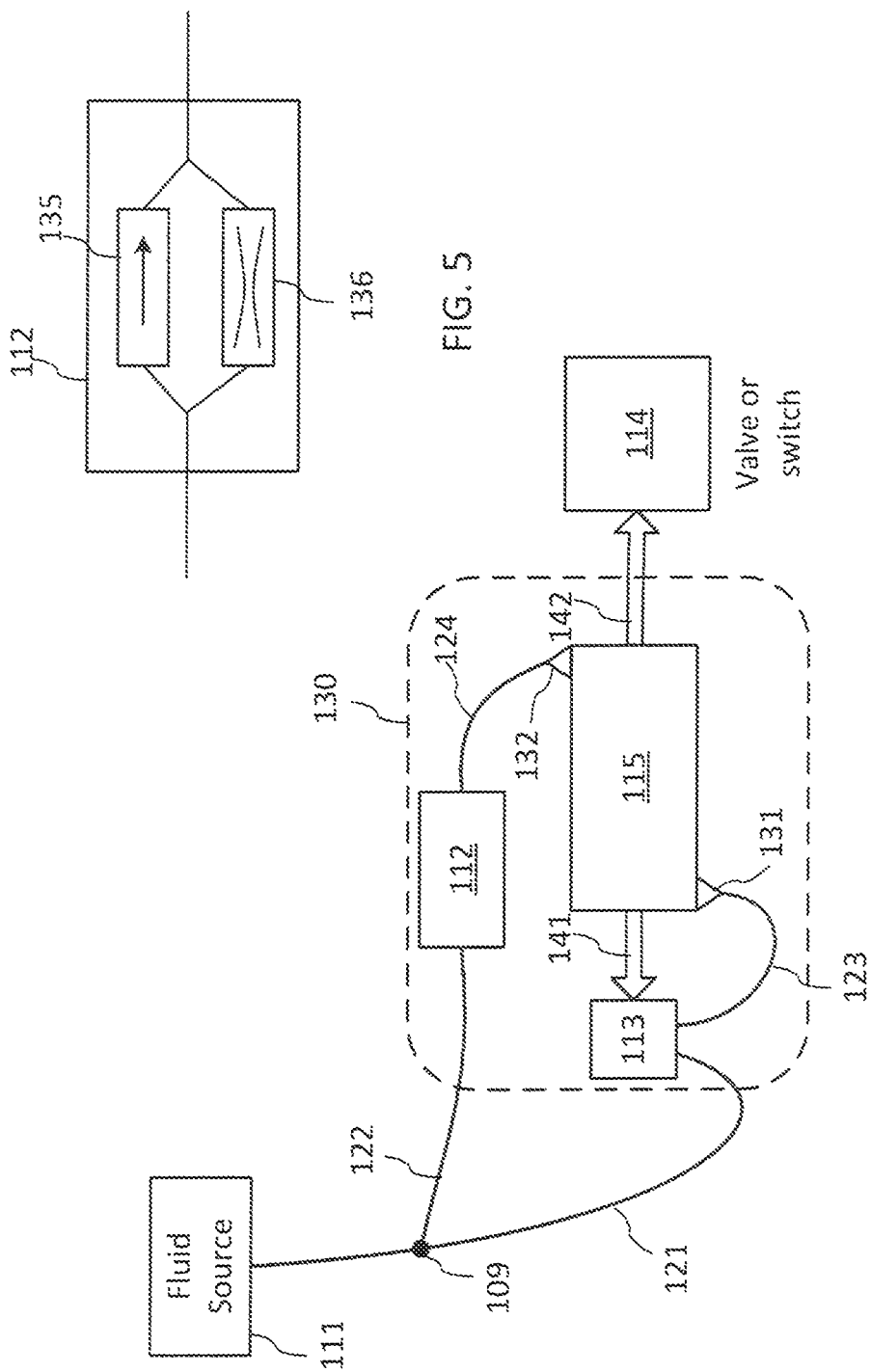

FLUID-OPERATED APPARATUS, METHOD, AND CIRCUIT

CROSS-REFERENCE TO RELATED APPLICATIONS

The present invention claims priority from U.S. Provisional Patent Application No. 62/328,116 filed Apr. 27, 2016, which is incorporated herein by reference.

TECHNICAL FIELD

The present invention generally relates to a fluid-operated apparatus, method, and circuit that is configured to activate or de-activate an on-demand function, and more particularly relates to a device that connects to an output of a pneumatic control valve controlling an air-driven tool, and provides the ability to add, subtract or augment a function to the tool from the same pneumatic control valve.

BACKGROUND OF THE INVENTION

Pneumatic tools, such as drills used in dental procedures, often are activated by a 3 way foot valve. Alternatively a trigger-actuated valve could be used. A light pressure on the foot valve will provide minimal torque to the drill for low torque 'feathering' operations while full foot pressure brings the drill to a maximum operating pressure. Drill tool manufacturers typically recommend pneumatic operating pressures. This operating pressure is assigned based on such considerations as heavy cutting requirements, turbine bearing stress and life of the turbine chuck that holds the bits and burs. This 'operating pressure' maintains the revolutions per minute (rpm) of the turbine bearings within component specifications even when it is running and not under load. Setting the maximum pressure above recommended pressure leads to chronic over revving of the drills and turbines in frequent and unnecessary situations resulting in premature tool failure. However, there is a need to have an ability to temporarily increase the drill speed for a short period of time, returning to a default speed when the action is completed. For example, such situations might be the cutting away of an old amalgam filling from a tooth. There may also be other situations when temporarily adding, subtracting, or augmenting a function of a tool in a default operating state is desirable. On the other hand, having to manually increase the drill pressure for apropos situations and then reset is, or otherwise having to use several different controls to control different functions, is not feasible or at least desirable under typical use.

SUMMARY OF THE INVENTION

An object of the present invention is to provide a technique, and an apparatus or circuit implementing it, which may be used to temporarily add, subtract, or augment a function to a fluid-control system, instrument, or tool from a same fluid control element that controls the default operation of the system, instrument, or tool.

Another object of the present invention is to provide an apparatus and method that is capable of operating a switch or a valve in a fluid-controlled system by a short-term drop in a fluid pressure in the system.

One aspect of the disclosure provides a fluid-operated apparatus that responds to a pressure signal, which may be in the form of a brief drop or interruption in supplied fluid pressure, by switching from a standby state or mode to an active state or mode, and which may return to the standby state or mode when the supplied fluid pressure drops for a longer period of time, so that the system may restart in the default mode. The apparatus may be used to controllably activate or deactivate a function using a switch or a valve that is coupled to the apparatus or is a part thereof so that a transition of the apparatus from the standby state or mode to the active state or mode changes the state of the switch or valve, for example from an open to closed or vice versa. The apparatus can be used to add, subtract, or augment a function related to the operation of a pneumatic or hydraulic tool utilizing the control valve that regulates the supply of fluid pressure to the tool.

An aspect of the present disclosure provide an apparatus for activating an on-demand function, the apparatus comprising a fluid-operated bistable circuit (FOBC) with one or more circuit ports configured to be pressurized by connecting to a source of fluid under pressure. The FOBC may be configured to operate in a standby mode when the one or more circuit ports are pressurized by the fluid after being depressurized for at least a first time interval, to switch or transition to an actuating mode when the one or more circuit ports are briefly depressurized for a time interval shorter than the first time interval and then pressurized again, and to return to the standby mode from the actuating mode if the one or more circuit ports remain depressurized for a time interval longer than the first time interval. The FOBC may further be configured to actuate a function-activating valve or switch when in the actuating mode, wherein the function-activating valve or switch is operational to activate the on-demand function.

In accordance with at least some embodiments of the apparatus, the one or more circuit ports may comprise a first valve and a flow control module, wherein the first valve is open in the standby mode and closed in the actuating mode. The FOBC may include a fluid-operated biased actuator (FOBA) comprising a first actuator port and a second actuator port, said first and second actuator ports being independently pressurizable by the fluid received from the first valve and from the flow control module, respectively, wherein the FOBA is configured to be actuated by a pressure imbalance between the first and second actuator ports. The FOBA may be operatively coupled to the function-activating switch or valve for actuating thereof in response to an excess fluid pressure at the second actuator port relative to the first actuator port that exceeds a first threshold.

The FOBA may be operatively coupled to the first valve for closing thereof in response to the excess fluid pressure at the second actuator port that exceeds a second threshold that is equal or smaller than the first threshold, wherein the first threshold is equal or smaller than the excess fluid pressure at the second actuator port when the one or more circuit ports are all pressurized and the first valve is closed. The flow control module may be configured to throttle a back flow of the fluid from the second actuator port when the one or more circuit ports are depressurized so as to cause the second actuator port to depressurize more slowly than the first actuator port and to at least temporary cause the excess fluid pressure at the second actuator port to exceed the second threshold, thereby actuating the FOBA to close the first valve.

One aspect of the present disclosure provides an apparatus for activating an on-demand function in a circuit comprising a three-way control valve configured to control the delivery of fluid under pressure, the apparatus comprising: a fluid-operated biased actuator (FOBA) comprising a first actuator port and a second actuator port, said first and second actuator ports being independently pressurizable by the fluid, the FOBA configured to be responsive to an excess fluid pressure at the second actuator port relative to a balanced relationships with the first actuator port; a first fluid supply line for connecting the first actuator port to the output of the 3-way control valve, the first fluid supply line comprising a first valve that is operatively coupled to the FOBA; and a second fluid supply line for connecting the second actuator port to the output of the 3-way control valve, the second fluid supply line comprising a flow control module. The first valve, when open, permits the fluid from the three-way control valve to pressurize the first actuator port when the first three-way control valve is activated, and, when closed, blocks or at least restricts the fluid from pressurizing the first actuator port. The FOBA may be configured to actuate a function-activating valve or switch for activating the function when the excess fluid pressure at the second actuator port exceeds a first threshold. The FOBA may further be configured to control the first valve responsive to the excess pressure at the second actuator port, so as to keep the first valve open when the first and second actuator ports are pressure-balanced, and to close the first valve when the excess fluid pressure at the second actuator port exceeds a second threshold that is equal or smaller than the first threshold. The flow control module may be configured to throttle a back-flow of the fluid from the second actuator port, so as to cause the second actuator port to depressurize more slowly than the first actuator port when the three-way control valve is disengaged by the operator, thereby causing the FOBA to at least temporary close the first valve for a first time interval and to open the first valve after the first time interval is expired if the three-way valve remains disengaged. The FOBA actuates the function-activating valve or switch if the control three-way valve is re-engaged while the first valve remains closed.

Another aspect of the present disclosure provides a method to activate an on-demand function in a circuit during normal operation thereof, the circuit comprising a 3-way control valve configured to control the delivery of fluid under pressure to an instrument, the method comprising: tapping an output of the 3-way control valve to a fluid-operated bistable circuit (FOBC) configured to transition from a standby mode to an actuating mode by a drop of input fluid pressure lasting shorter than a first time interval, and to return to the standby mode if the drop lasts longer than the first time interval; and, coupling the FOBC to a function-activating valve or switch for actuation thereof when the FOBC is in the actuating mode, wherein the function-activating valve or switch is configured to activate the on-demand function.

BRIEF DESCRIPTION OF THE DRAWINGS

The invention will be described in greater detail with reference to the accompanying drawings which represent preferred embodiments thereof, which are not to scale, in which like elements are indicated with like reference numerals, and wherein:

FIG. 4 is a schematic block diagram illustrating an embodiment of the fluid-operated apparatus of FIG. 2 wherein a biased two-port actuator receives pressurized fluid from a common source via a valve and a flow control module and wherein the actuator controls the valve responsive to a pressure balance at actuator ports;

FIG. 5 is a schematic block diagram of one embodiment of a flow control module that may be used in a dynamically-bistable fluid operated apparatus for activating an on-demand function;

FIG. 14 is a schematic diagram of an embodiment of the fluid operated bistable circuit including a single-ended cylinder actuator configured to actuating a first valves in one state and a second valve or a switch in another state;

FIG. 15 is a schematic diagram of an embodiment of the fluid operated bistable circuit including a single-ended cylinder actuator configured to simultaneously engage two valves, or a valve and a switch in one state and to disengage from both in another state.

DETAILED DESCRIPTION

Exemplary embodiments of the present disclosure may be described hereinbelow with reference to air-driven dental tools and/or instruments. However, it will be appreciated that various aspects of the present invention are applicable to any tool or device that is driven by pressurized fluid, including various pneumatic and hydraulic tools or instruments. In at least some of the embodiments the fluid-driven tool is operated using a 3-way valve that can turn on or off the supply or fluid pressure to the tool. The term 3-way valve is used herein to refer to a valve having an input port for connecting to an input supply line for supplying pressurized fluid and an output port for connecting to an output supply line, and which permits the output supply line to depressurize when the valve is closed. Furthermore, at least some of the example embodiments described hereinbelow are described with reference to a fluid-controlled system wherein the fluid is air, such as a pneumatic system for operating an air-driven tool, wherein the supply of air to the tool is controlled by a foot-operated 3-way valve; where the operator typically activates the valve by stepping on it to open the valve thereby permitting the pressurized air to reach the tool, and deactivates the valve by removing the foot pressure from the valve to close it, thereby turning the tool off while allowing the pressurized air to be drained back through the valve. It will be appreciated though that the principles and features described herein apply also to tools and devices that are driven by fluids other than air, such as hydraulic systems and tools, and to control elements or valves other than foot valves, including but not limited to electrically controlled valves.

Figure 1:
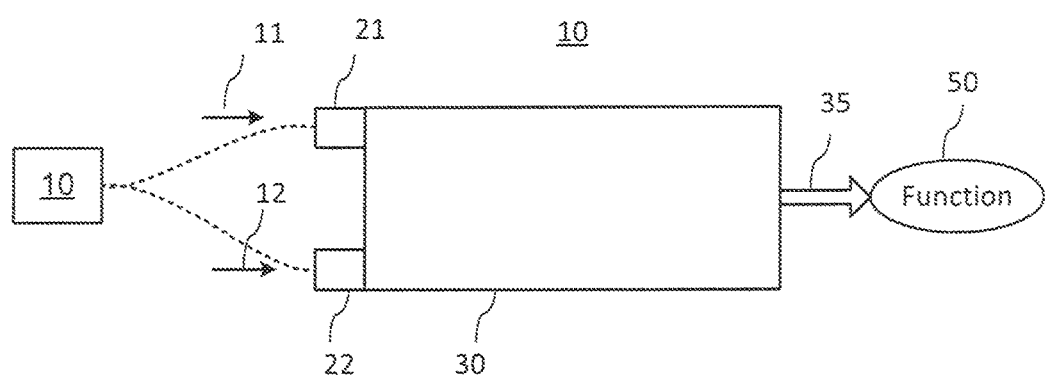
FIG. 1 is a schematic diagram illustrating a fluid-operated dynamically bistable apparatus with two input ports for activating and/or deactivating an on-demand function responsive to a pressure signal.

Turning first to FIG. 1, there is generally represented an apparatus 10 for activating an on-demand function 50 in response to a pressure signal according to an embodiment of the present disclosure. Apparatus 10 includes a fluid-operated bistable circuit (FOBC), schematically represented by a block 30, having two fluid input/output ports 21 and 22, which may be referred to as the first and second circuit ports 21, 22 and each of which configured to be pressurized by connecting to a source of fluid under pressure. In a typical operation scenario they may be connected to a common source 10 of pressurized fluid, as schematically represented in the figure by dotted connection lines. Accordingly, in one embodiment the first and second circuit ports 21, 22 may be internal to the apparatus 10, both connecting internally to a common input/output port of the apparatus (not shown in FIG. 1). FOBC 30 is configured to be switchable in operation from a standby state or mode to an active, or actuating, state or mode by a fluid pressure signal at the input ports 21, 22. In at least some embodiments FOBC 30 is further configured to switch back to the standby mode soon after the pressure signal ceases and/or first and second input ports 21, 22 are depressurized; accordingly in such embodiments FOBC 30 may be referred to as dynamically bistable as its active or actuating mode may be stably operational only when energized by fluid pressure. In one embodiment, the pressure signal may be in the form of a brief drop in the fluid pressure received at the input ports 21, 22, and FOBC 30 is configured to respond to that signal by switching to the actuated state. In one embodiment FOBC 30 may be configured to be in a standby mode when the first and second circuit ports 21, 22 are both pressurized by the fluid, after being both depressurized for at least a first time interval $\Delta t_1$, and to switch from the standby mode to an actuating mode when the first and second circuit ports 21, 22 are briefly depressurized for a time interval shorter than the first time interval $\Delta t_1$, returning to the standby mode if the first and second circuit ports remain depressurized for a time interval longer than the first time interval.

Figure 3:
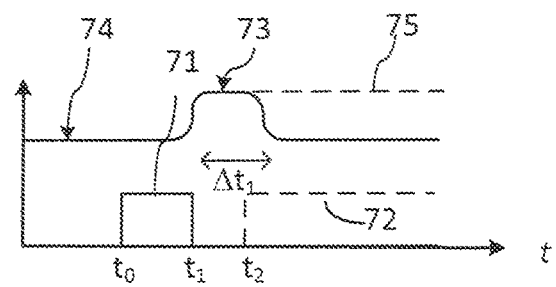
FIG. 3 is a time diagram illustrating the operation of the apparatus of FIG. 1 or 2 in one embodiment thereof.

This operation of FOBC 30 is schematically illustrated in the time diagram of FIG. 3 where line 71 represents the fluid pressure at ports 21 and 22, and line 74 represents the standby mode of FOBC 30. Prior to time instance $t_0$, ports 21, 22 are not pressurized, i.e. do not receive pressurized fluid, and FOBC 30 may be in the standby mode. At time $t_1$ the pressure at ports 21, 22 is turned on, and FOBC 30 either remains in, or switches to, the standby mode 74. At time $t_1$ the pressure at ports 21, 22 drops, for example but not necessarily down to the ambient pressure, which causes FOBC 30 to transition to a temporary state or mode 73, possibly after a short transition time, for example a few tenth of a second or less. If the fluid pressure at ports 21, 22 is not reinstated within a pre-defined first time period $\Delta t_1$, FOBC 30 transitions back to the standby mode 74. If the fluid pressure at ports 21, 22 is turned on again within the pre-defined first time period $\Delta t_1$, for example at time $t_2$ where $(t_2-t_1)<\Delta t_1$, as illustrated by the dashed line 72, FOBC 30 the transitory state 73 of FOBC 30 becomes, or transitions to, an actuating state or mode, as illustrated by the dashed line 75, in which it may activate function 50. Thus, FOBC 30 reacts to a pressure signal in the form of a brief drop in the input fluid pressure by switching from the standby mode to the activating mode. Furthermore FOBC 30 may return to the standby mode when the input pressure ceases for a longer time interval. Accordingly, FOBC 30 may be said to be a bistable circuit or device that has a dynamic short-term memory, and remembers input pressure for a pre-determined, typically brief, time period $\Delta t_1$, whereby FOBC 30 temporarily operates in a waiting regime after the drop in input pressure.

FOBC 30 may be configured to activate function 50 when in the actuating mode, as schematically illustrated in FIG. 1 by the arrow 35. This may include, for example, providing FOBC 30 with a coupling 37 that may be configured to turn on or off a switch or a valve 40 when FOBC 30 is in actuating mode, as schematically illustrated in FIG. 3 and described hereinbelow in further detail with reference to example embodiments. Accordingly, function 50 may be temporary activated simply by briefly interrupting the supply of pressurized fluid to FOBC 30 for a short interval, which may be accomplished from the same control element that controls the delivery of the pressurized fluid to the system employing apparatus 10, and in at least some embodiments may be de-activated again by turning off the supply of pressurized fluid for a longer time period. In a typical embodiment function 50 may be an on-demand function which may be temporarily activated by an operator or a control system during normal operation of an instrument when situation demands.

Figure 2:
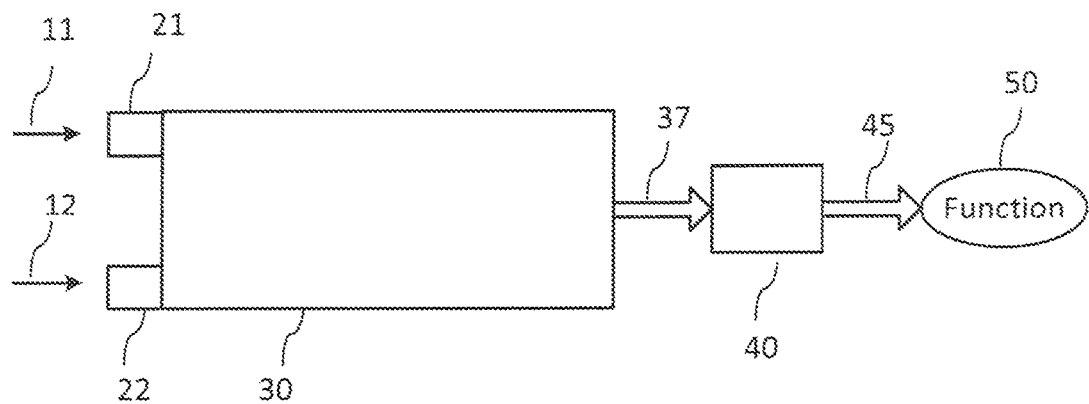
FIG. 2 is a schematic diagram illustrating the two-port fluid-operated apparatus of FIG. 1 coupled to a function-activating device.

Referring now to FIG. 4, there is presented a block diagram of an embodiment of the apparatus 10 of FIG. 1 or 2 where FOBC 30 is implemented in the form of a dynamically-bistable FOBC 130 that includes a double-action fluid-operated bistable actuator (FOBA) 115 having a first actuator port 131 and a second actuator port 132. FOBA 115 may be in a default state and in an activated state. Valve 113, which may also be referred to herein as the first port valve or simply as the first valve, is connected to the first actuator port 131 by a pressure-tight fluid line 123. A flow control module (FCM) 112 connects to the second actuator port 131 by a pressure-tight fluid line 124. Each of the first and second actuator ports 131, 132 is configured to be pressurized independently from the other actuator port by receiving fluid under pressure from valve 113 or flow control nodule 112. In operation valve 113 and flow control module 112 may be connected to a common source of pressurized fluid 111, for example using pressure-tight fluid lines 121, 122 and a common port 109. First port valve 113 may embody, or be a part of, the first input port 21 of FOBC 30 of FIG. 1 or 2, while FCM 112 may embody, or be a part of, the second input port 22 of FOBC 30 of FIG. 1 or 2. Fluid lines 121, 122 may also be referred to herein as the first and second input fluid lines, respectively; when included, they may be viewed as constituent parts of the first and second input ports of the FOBC 130, respectively.

Valve 113 is controlled by FOBA 115 using valve coupling 141, and is open to the flow of pressurized fluid in both directions when FOBC 130 is in its standby mode. FOBC 130 is in the standby mode when valve 113 is open and FOBA 130 in its default state. When FOBC 130 is in its actuating mode valve 113 is closed and the second actuator port 132 is pressurized by receiving pressurized fluid from the fluid source 111.

In one embodiment FOBA 130 is configured to activate an on-demand function, for example using coupling 142 that acts on a function activating switch or valve 114, in response to an excess fluid pressure at the second actuator port 132 relative to the first actuator port 131, if the excess fluid pressure exceeds a first threshold $\Delta P_1$. The first threshold $\Delta P_1$ may be equal or smaller than the excess fluid pressure at the second actuator port 132 relative to the first actuator port 131 when the second actuator port 132 is pressurized by the fluid from the fluid source 111 while the first actuator port 131 is fully depressurized, that is when the first input line 121 is depressurized and the pressurized fluid is permitted to escape FOBA 130 from the first port 131. Couplings 141 and 142 may be commonly referred to herein as the actuator coupling.

In one embodiment FOBA 130 is configured to close the first valve 113 in response to a pressure imbalance between actuator ports 131 and 132 in the form of an excess fluid pressure at the second actuator port 132 relative to the first actuator port 131, if the excess fluid pressure exceeds a second threshold $\Delta P_2$ that is equal or smaller than the first threshold $\Delta P_1$. In one embodiment FOBA 130 may be configured to be biased so that it is sensitive to an excess pressure at the second actuator port 132 relative to the first actuator port 131 and is insensitive to an excess pressure at the first actuator port 131. In one embodiment FOBA 130 is configured to open the first valve 113 when the first and second actuator ports 131, 132 are pressure-balanced, for example both substantially equally pressurized or both substantially equally depressurized.

In one embodiment the flow control module 112 may be configured to restrict, for example throttle, a back flow of the fluid from the second actuator port 132 when the fluid line 122 is depressurized. The back flow restriction in the flow control module 112 may be configured so that when the first and second input fluid lines 121, 122 are simultaneously depressurized, the second actuator port 132 depressurizes more slowly than the first actuator port 131, so as to at least temporary, for the duration of the first time period $\Delta t_1$, cause relative excess of fluid pressure $\Delta P$ at the second actuator port 132 over the first actuator port 131 to exceed the second threshold $\Delta P_2$, thereby activating FOBA 130 to close the first valve 113. Re-pressurizing the first and second input fluid lines 122, 121 within the first time interval, while the first valve 113 is closed, causes the pressurized fluid to charge second port 132 through FCM 112 rising the excess pressure at the second actuator port 132 relative to the first actuator port 131 to a level exceeding the first threshold $\Delta P_1$, which is so selected, thereby causing FOBA 115 to activate the on-demand function, for example by means of coupling 142 actuating the switch or valve 114. If the first and second input fluid lines 122, 121 are not re-pressurized within the first time interval, the second actuator port 132 de-pressurizes, thereby equalizing with the first actuator port 131, and causing FOBA 115 to return to its default state. In one embodiment the valve coupling 141 may be configured to open valve 113 when FOBA in the default state, thereby causing FOBC 130 to return to the standby mode wherein valve 113 is open and FOBA 115 is in it default state.

With reference to FIG. 5, in one embodiment the flow control module 112 may include a flow check valve 135 and a flow restrictor 136 connected in parallel. The flow check valve 135 is configured to permit a substantially unrestricted flow of the fluid in a forward direction from the second input fluid line 122 to the second actuator port 131, as illustrated by the arrow, while substantially blocking the fluid back flow out of the second actuator port 132. The flow restrictor 136 is configured to throttle the fluid back flow from the second actuator port 132 so as to slow it down when the second input fluid line 122 is depressurized. The degree of throttling determines the duration of the first time interval $\Delta t_1$ during which first valve 113 is closed by FOBA 115 after the input lines 121, 122 are depressurized keeping FOBC in the waiting mode, and may be selected depending on application. By way of example, the flow restrictor 136 may be selected so that $\Delta t_1$ is in the range from a fraction of a second to a few seconds, for example in the range 0.5-5 seconds.

Figure 6:
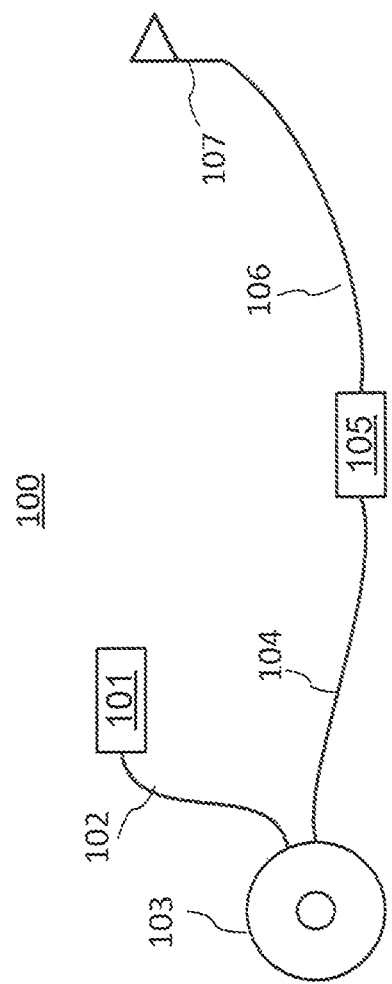
FIG. 6 is an example prior-art circuit using a 3-way control valve for supplying a fluid-operated tool with pressurized fluid through a flow restrictor.

Referring now to FIG. 6, there is schematically illustrated a simplified diagram of a fluid supply circuit 100 for operating a fluid-driven tool 107. The circuit 100 includes a source of pressurized fluid 101 that connects to an input port of a 3-way valve 103 with a fluid line 102. The output port of the 3-way valve 103, which may also be referred to herein as the 3-way control valve or simply as the control valve, connects to tool 107 by means of fluid lines 104, 106 and an optional flow restrictor or regulator 105. The fluid supply lines 102, 104, and 106 are pressure-tight so as to supply the fluid pressure to tool 7 when in operation, and may be for example in the form of suitable pneumatic or hydraulic supply tubing.

Generally the fluid that drives tool 107 may be in the form of a liquid or a gas, but for the sake of specificity and by way of example the description hereinbelow will be mostly with reference to an air-driven tool 107. Further by way of example, tool 7 may be in the form of, or include, a handpiece, such as a dental drill, and the 3-way valve 103 may be a foot-operated pneumatic valve, which may be referred to herein as the foot valve, and which permits the operator to control the flow of air while operating the handpiece 107. In such embodiments, the source of pressurized fluid 101 is a compressed air source, which may be regulated, and which in operation constantly supplies the foot valve 103 via supply tubing 102 with compressed air under pressure. When the foot valve 103 is activated, i.e. engaged by the operator, the compressed air flows from the compressed air source 101 and the foot valve 103, charging the output tubing 104 where it proceeds through the optional flow restrictor or regulator 105 that may throttle the compressed air to a desired pressure for the pneumatic handpiece or tool 107 via the hand tool tubing 106.

Figure 7:
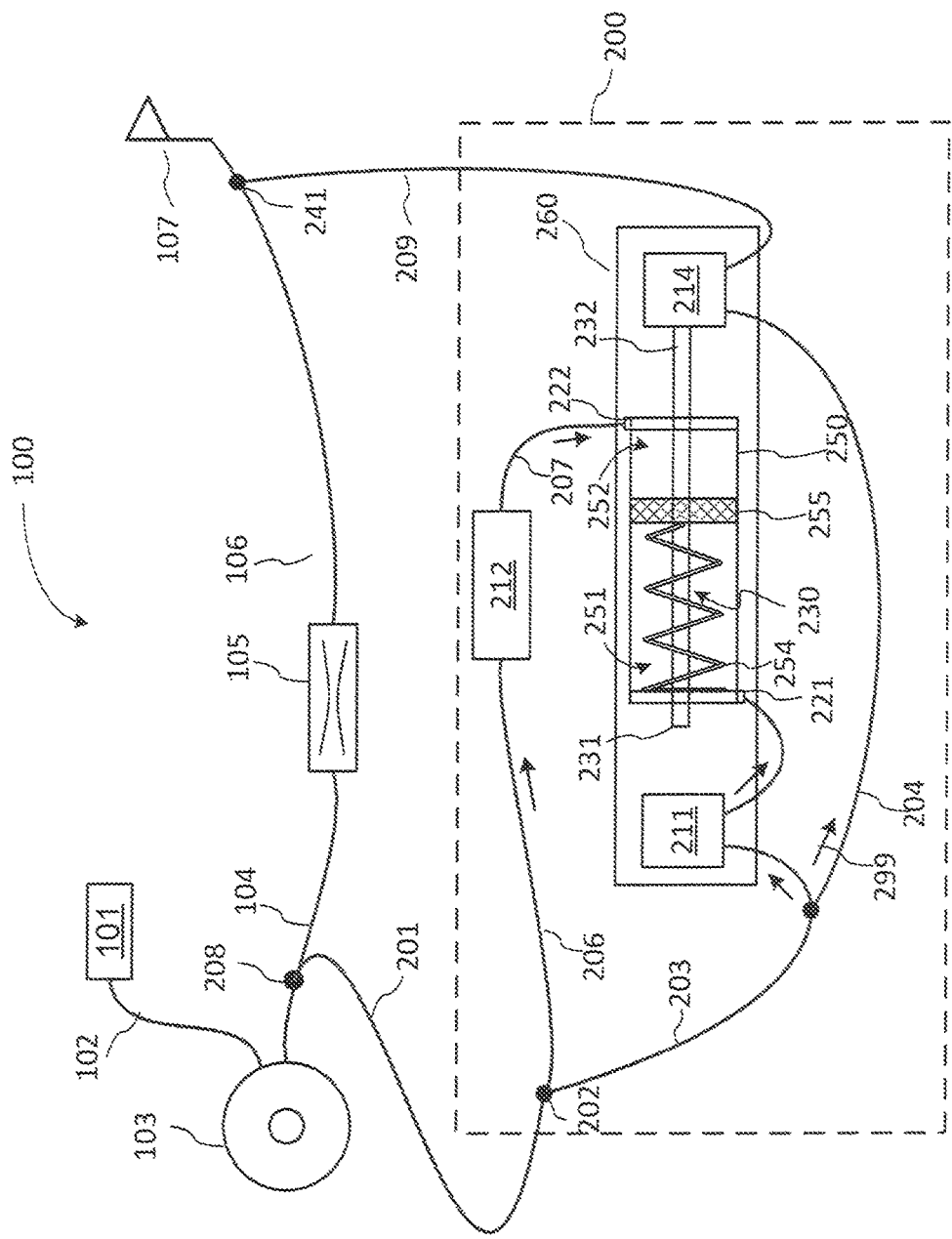
FIG. 7 is a schematic diagram illustrating a fluid supply system wherein an embodiment of the fluid-operated apparatus of FIG. 4, with a spring-biased double-sided pneumatic cylinder actuator, is connected to the tool fluid supply line of FIG. 6 in parallel with the flow restrictor; the spring-biased double-sided pneumatic cylinder actuator, which is detailed in a exposed mode to facilitate understanding, is in a default state preventing the pressurized fluid from circumventing the restrictor.

Turning now to FIG. 7, there is illustrated an ancillary fluid-operated circuit 200 connected to the fluid-supply circuit 100 in parallel with flow restrictor 105 to enable activating or de-activating an on-demand function of revving up tool 107 from the same 3-way control valve 103 that controls the supply of the fluid to the tool 107 during normal operation thereof. When activated by a pressure signal from 3-way control valve 103, circuit 200 provides a predetermined increase in fluid pressure to tool 107. In the illustrated embodiment circuit 200, when actuated by a pressure signal from control valve 103, permits the pressurized fluid, such as compressed air, to circumvent the flow restrictor 105 by opening or closing activation valve 214, which in this embodiment implements the function-activating valve or switch 114 of FIG. 4 and may also be referred to herein as the second valve. When activation valve 214 is open and control valve 103 is activated pressurizing its output supply line 104, the compressed air from source 101 flows through the auxiliary circuit 200 via divider 208, common input fluid supply line 201, first input fluid supply line 203, supply line 204 that circumvents valve 211 and actuator 250, activation valve 214, and output fluid supply line 209, re-entering the hand tool fluid supply line 106 via divider 241, thereby adding air pressure to the tool through circuit 200 circumventing air restrictor 105. FIG. 7 illustrates the system during normal operation thereof, with circuit 200 in a standby mode where valve 214 is closed.

Circuit 200 may be viewed as an embodiment of FOBC 130 of FIG. 4, with valve 211 embodying the first valve 113 and a flow control module (FCM) 212 embodying the flow control module 112, each operating generally as described hereinabove with reference to valve 113 and FCM 112, respectively, and FIGS. 4 and 5. Valve 211, which may be referred to hereinafter as the first port valve, and FCM 212 are commonly connected to the output of the control valve 103 via divider 208, common input fluid supply line 201, and divider 202, with first and second input fluid supply lines 203 and 206 directing the compressed air, or generally pressurized fluid, to valve 211 and FCM 212, respectively. Valve 211 controls the flow of compressed air from the control valve 103 to a first port 221 of actuator 250, while the flow control module 212 controls the flow of compressed air from the control valve 103 to a second port 222 of actuator 250. Actuator 250, which may be an implementation of FOBA 115 of FIG. 4, is in it default state when actuator ports 221, 222 are substantially pressure-balanced, for example both pressurized by compressed air from control valve 103 or are both depressurized, such as when control valve 103 is disengaged allowing fluid supply lines 201, 206, and 203 to depressurize and compressed air to escape from both chambers of the actuator 250 through fluid supply lines 201, 206 and 203. Actuator 250 may be switched from its default state, in which it keeps valve 214 closed, to an activated state in which it lets valve 214 to open, by a pressure imbalance at its ports 221, 222. Valves 211 and 214 may be mounted mechanically onto actuator 250 or the two valves 211, 214 and actuator 250 are anchored individually, in appropriate relative positions, onto a common frame 260, so that actuator 250 can engage either one of valves 211 and 214 to change their state, depending on the actuator's state. A basic on-off valve will suffice for valve 211 and for valve 214.

Each of valves 211, 214 may be closed when engaged by actuator 250 but open otherwise, or may be open when engaged by actuator 250 but closed otherwise. In other embodiments one of valves 211, 214 may be open when engaged and another closed when engaged, and the actuator may be configured to engage or disengage both of them at the same time. When open, valve 214 permits the compressed air from the control valve 103 to flow there through, entering tool supply line 241 and revving tool 107, for example to a higher rpm when tool 107 is a pneumatic drill. When closed, valve 214 blocks the flow of compressed air through FOBC 200 into supply line 106 of tool 107. In the example embodiment illustrated in FIG. 7 valves 211 and 214 are normally open unless engaged by actuator 250, one at a time. By way of example, each of valves 211 and 214 may be a mechanically actuated push button momentary valve.

Continuing to refer to FIG. 7, in the illustrated embodiment actuator 250 is in the form of a double-ended double-action pneumatic cylinder enclosing piston 255. Piston 255 divides the cylinder cavity into two pressure-tight chambers, a first chamber 251 with the first port 221 and a second chamber 252 with the second port 222. Each of the first and second ports 221, 222, which may also be referred to herein as the first and second actuator ports, provide conduits allowing compressed air to either enter, or be released from the respective chamber of the actuator 250 at one side thereof. Piston 255 is movable axially within the cylinder by a balance of fluid pressure in the first and second chambers 251 and 252, as determined by a balance of pneumatic fluid pressures at the first and second ports 221, 222. Note that the term 'cylinder' as used herein does not require a circular cross-section, and actuator 250 may generally be a hollow member defining a pressure-tight cavity of any suitable cross-section that permits a piston enclosed therein and dividing the cavity into two pressure-tight chambers to be movable within the cavity responsive to a pressure imbalance on both sides thereof.

A piston rod 230 is fixedly attached to piston 255 and is axially movable therewith. Piston rod seals may be provided at each end of the actuator 250 in some actuator designs to contain the pressurized fluid within the chambers 251, 252 while permitting the axial motion of the piston rod 230, or the same objective may be achieved by other suitable means. Piston rod 230 has a first end 231 for engaging valve 211, and a second end 232 for engaging valve 214; in the illustrated embodiment only one of these valves can be engaged by rod 230 at a time. The first end 231 of rod 230 implements valve coupling 141 of FOBC 130 illustrated in FIG. 4, while the second end 231 of rod 230 implements the second coupling 142 of FOBC 130. Piston rod 230 may be a one-piece rod bonded in place through piston 250 or two separate pieces bonded either side of piston 250. Actuation of valves 211, 214 is thus controlled via position of piston 255 and piston rod 230, with piston rod 230 providing the push, pull or disengagement force the particular valve design requires for valve actuation.

Piston 255 is biased with a spring 254, which acts upon piston 255 to push it and rod 230 towards a default position, which may mean pushing towards either valve 214 or valve 211, depending on whether valves 211, 214 are normally open or closed, and as defined by the spring position within the actuator cylinder. In the illustrated embodiment valves 211 and 214 are normally open, and spring 254 is positioned so that when fluid pressure at port 222 is at least balanced by fluid pressure at port 221, actuator 250 is in the default position wherein spring 254 pushes piston rod 230 to engage second valve 214 so as to close it while being disengaged from valve 211 keeping it open. The standby mode of circuit 200, with the actuator 250 in the default state, first port valve 211 open and function-activating valve 214 closed, is illustrated in FIG. 7, where arrows 299 illustrate air flow when 3-way valve 103 is activated.

Figure 8:
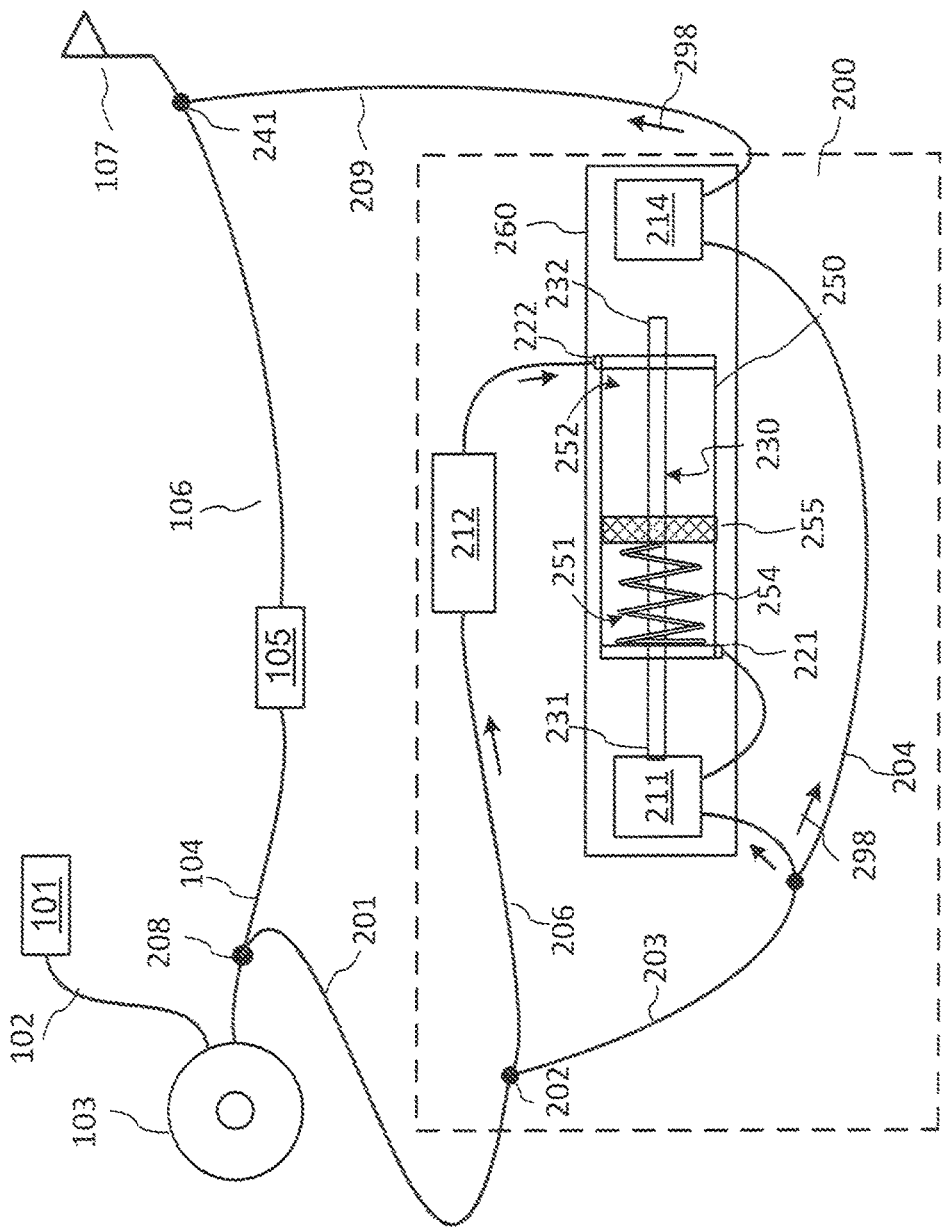
FIG. 8 is a schematic diagram illustrating the fluid supply system of FIG. 8 with the actuator in an activated stated permitting the pressurized fluid to circumvent the restrictor.

Referring now also to FIG. 8, when the 3-way control valve 103 is deactivated by an operator, a loss of input pressure may initiate a state transition in circuit 200 wherein valve 211 is initially open, permitting compressed air from port 221 to escape actuator 250 quicker than from port 222 where FCM 212 restricts the backflow, resulting in an excess pressure at port 222. This excess pressure is temporary and dissipates when all compressed air or, generally, pressurized fluid, escapes from the second chamber 252 through port 222 and FCM 212. FCM 212 and spring 254 may be selected so that for a desired duration of time $\Delta t_1$ this temporary excess pressure at port 222 relative to port 221 exceeds a threshold pressure imbalance $\Delta P_1$ that overcomes the spring bias and, with a sufficient volume of the second chamber 252 and air volume in fluid supply line 207, pushes piston 255 into an activated position where it engages valve 211 to close it, while disengaging valve 214 to open it. FIG. 8 illustrates circuit 200 with actuator 250 in the activated state. Circuit 200 remains in a transitory 'waiting' mode of operation, with valve 211 closed and valve 214 open, for the duration of the first time interval $\Delta t_1$. Re-activation of control valve 103 while circuit 200 remains in the transitory 'waiting' mode permits compressed air to charge through valve 214 to enter the input air supply line 106 of tool 107, revving tool 107, while also reinforcing the fluid pressure imbalance between the actuator input ports 221, 222. The flow of compressed air through circuit 200 in its actuating mode is illustrated in FIG. 8 by arrows 298.

If 3-way valve 103 remains deactivated and input fluid supply lines 201, 203 and 206 depressurized for duration of time exceeding $\Delta t_1$, second actuator port 222 depressurizes too and the pressure imbalance between the first and second actuator ports decreases below the level required to overcome the biasing force of spring 254 to keep valve 211 closed, and actuator 250 relaxes to its default state, returning circuit 200 to its standby mode illustrated in FIG. 7, which will be maintained after re-engaging 3-way valve again.

If the operator reactivates 3-way valve 103 within the time interval $\Delta t_1$ while valve 211 is closed and circuit 200 is in the waiting mode, the flow of compressed air re-pressurizes port 222 but not port 221, thereby re-enforcing or at least maintaining the excess pressure at port 222, and keeping valve 214 open and the tool revving function activated until the operator disengages 3-way valve 103, allowing both actuator ports 221, 222 to depressurize and circuit 200 to return to its standby mode illustrated in FIG. 7.

Thus, connecting circuit 200 as an auxiliary circuit to fluid supply circuit 100 as illustrated in FIGS. 7,8 enables on-demand transitions from default pneumatic tool pressure to a predetermined increase in pneumatic tool pressure for particular situations. In embodiment wherein 3-way valve 103 is a foot valve, this can be done during the flow of the procedure by simply briefly releasing the foot control, for example for a fraction of a second, and re-engaging it. Conveniently, how quickly the foot control needs to be re-engaged may be configured by a suitable selection of flow control module 212 and in dependence on nominal operating system pressure. Furthermore, in at least some embodiments of circuit 200 that utilize non-latching valves 211, 214 the 'on demand' increase in pneumatic tool pressure will automatically disengage once the pneumatic tool is stopped by the release of the foot control. When re-engaged, the pneumatic tool 103 will once again operate at default pneumatic pressure until the 'on demand' feature is reactivated.

Advantageously, the use of FOBC 200 obviates revving of the pneumatic tool in unnecessary situations since the 'on demand' feature is only activated when need is imminent and immediately disengaged by the stopping of the tool. It is understood that when the pneumatic tool 107 is under load the RPM of the tool are modulated compared to the tool running without a load on it.

One feature of circuit 200 in the embodiments described hereinabove with reference to FIGS. 7 and 8 is that function-activating valve 214 is open in the transitory 'waiting' regime of the circuit before control valve is reactivated, which may potentially slow down the return of to a full system pressure in circuit 200 after re-activation of valve 103, as the compressed air will immediately charge through valve 214. This potential drawback may however be obviated for example by modifying circuit 200 to use normally closed momentary valves for valves 211 and 214, and flipping actuator 250 by 180 degrees so that rod 230 engages the first port valve to open it in the default position and the function-activating valve to open it in a fully actuated position, but permitting the function-activating valve to remain closed in the transitory 'waiting' state while the circuit is not yet re-pressurized; an embodiment with two normally closed valves is illustrated for example in FIGS. 10, 11 and 13 described hereinbelow.

It will be appreciated that providing an on-demand increase in pneumatic or hydraulic pressure is not the only on-demand function that can be activated or deactivated in a manner described hereinabove using various embodiments of FOBC 130 or FOBC 200, including functions that can be activated electrically rather than pneumatically or hydraulically, or generally by pressurized fluid. Furthermore, circuit 200 can be easily modified to use two momentary normally-closed valves, or one momentary normally-closed valve and one normally-open valve or switch, one momentary normally-open valve and one normally-closed valve or switch, or latching switches and/or valves.

Figure 9:
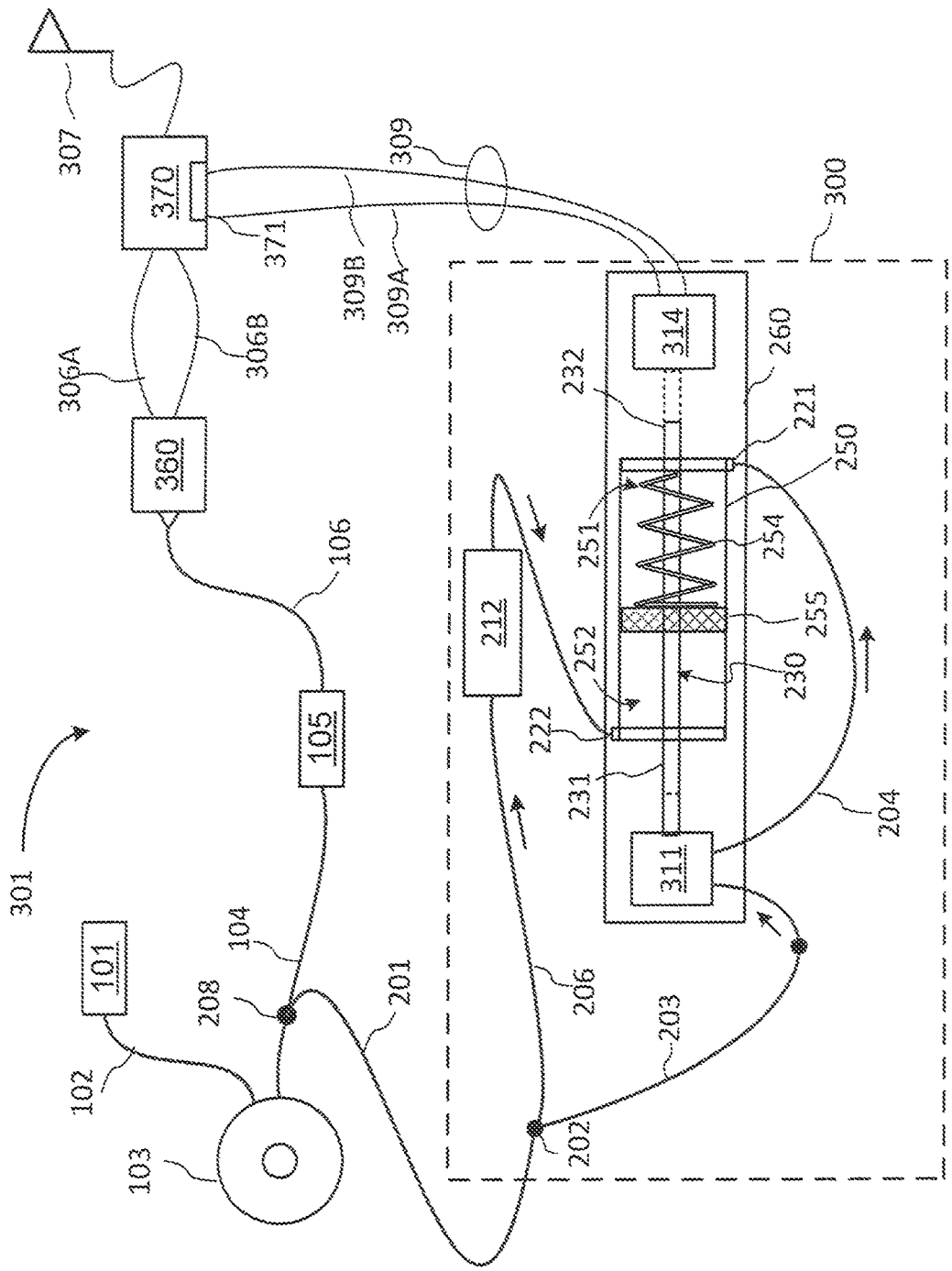
FIG. 9 is a schematic circuit diagram of a system wherein a bistable fluid-operated circuit with a spring-biased double-sided pneumatic cylinder actuator acts on a mechanically actuated electrical switch to activate or deactivate a boost function of an electric scaler in response to a pressure signal.

Turning now to FIG. 9, there is illustrated an example embodiment wherein auxiliary fluid-operated bistable circuit 300 is used to provide a temporary on-demand boost to an electric scaler 370, by turning on an electrical switch 314 that closes or breaks an electrical circuit 309 connected to a boost terminal of the scaler. Switch 314 may be, for example, a momentary mechanically-activated electrical push-button on/off switch. Elements in FIG. 9 that are functionally same or substantially similar to corresponding elements in FIGS. 7 and 8 are labeled with the same reference numerals and may not be described again. Here, a dental system 301 controlled by 3-way valve 103, which typically may be foot-activated, includes a pneumatically driven electrical switch 360 that is connected to scaler 370 with electrical leads 306A and 306B and, responsive to pneumatic pressure from the 3-way valve, turns on scaler 370 and activates handpiece 307 electrically connected thereto. Scaler 370 is a control module that may have an electric boost terminal 371 which, when electrically shorted, activates a scaler boost function. Circuit 300 represents another embodiment of FOBC 130, with valve 112 implemented using valve 311 which in this embodiment may be a 3-way valve, and function activating valve or switch 114 embodied with an electrical on/off switch 314.

In the illustrated embodiment valve 311 is normally closed unless engaged and actuated by actuator 250, and electrical switch 314 is OFF unless engaged and actuated by actuator 250. Accordingly, actuator 250 in circuit 300 is rotated by 180 degrees relative to its position in circuit 200, so that in its default state it is biased to engage valve 311 keeping it open while switch 314 is closed or OFF. Deactivation of the 3-way control valve 103 depressurizes first actuator port 221 via open valve 311 faster than second port 222, which air escape is slowed down by FCM 212, resulting in the transitory circuit state in which the excess pressure at the second port temporarily overcomes the spring bias and pushes piston rod 230 towards switch 314 and away from valve 311, closing valve 311. The circuit may stay in this transitory state for the duration of the first time interval $\Delta t_1$ while the excess pressure at port 222 relative to port 221 exceeds the first threshold $\Delta P_1$ defined by the strength of the spring. When valve 311 is a 3-way valve, compressed air continues to escape from port 221 while 3-way control valve 103 remains disengaged.

If the control valve 103 is re-engaged sometime during the first time interval when circuit 300 is in the transitory state while valve 311 is closed, compressed air from source 101 may re-pressurize port 222 to its full pressure, reinforcing the excess pressure at port 222 relative to port 221 causing it to exceed a second threshold $\Delta P_2$ that is sufficient to push piston rode 230 to a position where its second end 232 engages electrical switch 314 as illustrated by dotted lines in the figure, shorting boost terminal 371 via electrical connections 309A and 309B to activate the scaler boost function. Disengaging control valve 103 for a time interval sufficiently exceeding $\Delta t_1$ causes circuit 300 to relax to its default state wherein spring 254 pushes rod 230 to keep valve 311 open and switch 314 closed.

In some embodiments the excess pressure at port 222 may not exceed the second threshold $\Delta P_2$ while control valve 103 is disengaged, so that the function switch 314 is activated only when control valve 103 is quickly re-engaged reenergizing circuit 300 with compressed air, or generally pressurized fluid, while valve 311 is closed. In some embodiments, for example wherein switch 314 is positioned closer to actuator 250 and the second threshold $\Delta P_2$ is smaller, the pressure imbalance in the transitory state may be sufficient to cause rod 230 to engage switch 314 to actuate it and switch on, thereby activating the boost function of scaler 370 already in the transitory state of circuit 300.

Thus, circuit 300 enables an on-demand activation of the scaler boost function for a desired duration of time simply by briefly deactivating control valve 103 and quickly reactivating it again, for example within 0.5 to 1 second, or as defined by the first time interval $\Delta t_1$ that determines the lifetime of the transitory state of the circuit. Moreover, the boost function will automatically deactivate if the scaler is stopped by deactivating control valve 103 for a duration longer that the first time interval.

Figure 10:
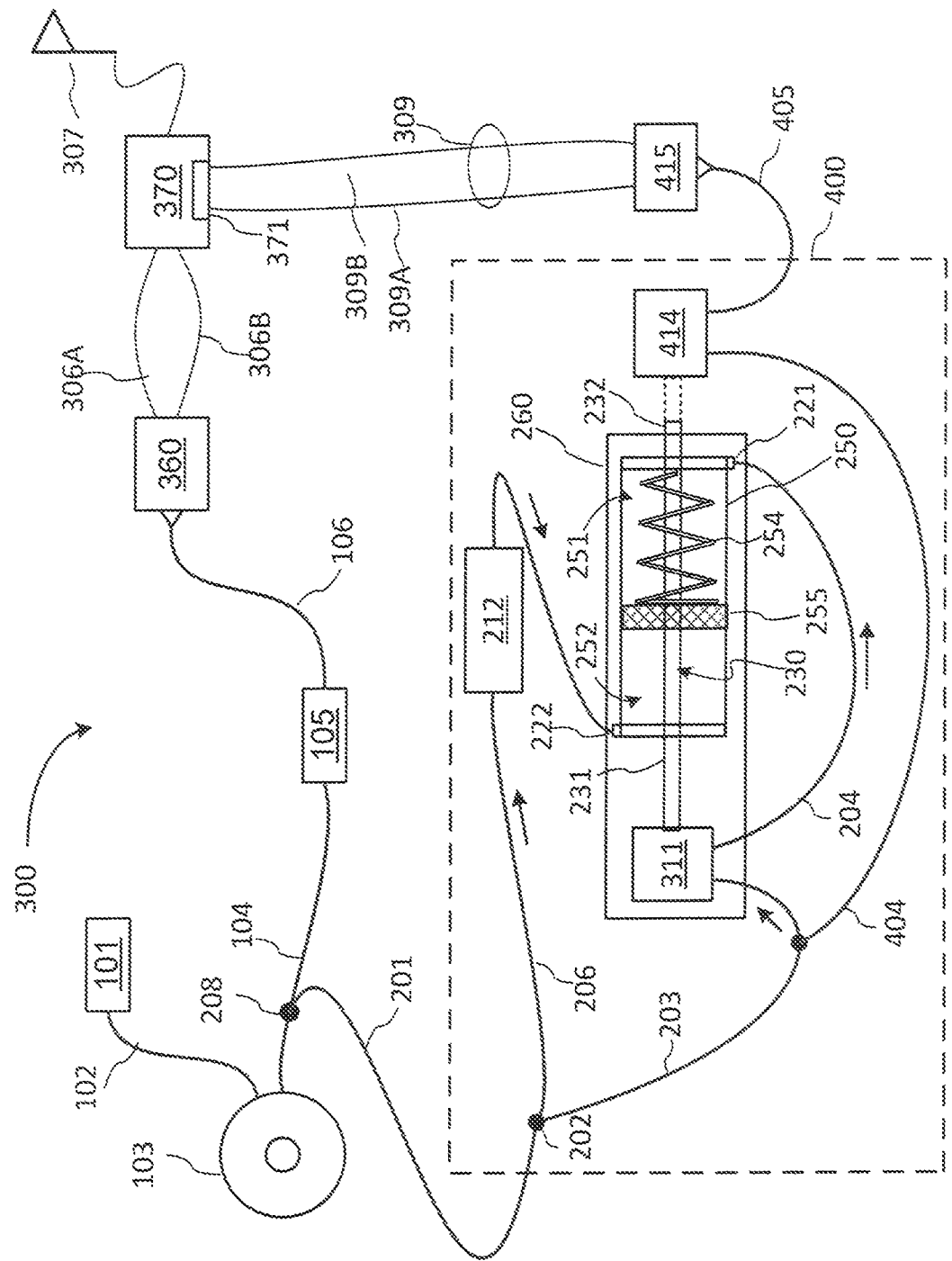
FIG. 10 is a schematic circuit diagram of an embodiment of the system of FIG. 9 with a valve coupled to a pneumatically actuated electrical switch replacing mechanically actuated electrical switch in the boost circuit of the scaler.

Turning now to FIG. 10, there is illustrated an embodiment of the dental scaler system of FIG. 9 wherein electrical on/off switch 314 is replaced with a valve 414, which may be a 3-way momentary valve and which output connects to a pneumatically operated electrical on/off switch 415 controlling the electrical boost circuit 309 similarly to electrical switch 314 in FIG. 9. Valves 311, 414 are both normally closed unless engaged by actuator 250. When actuator ports 221, 222 are pressure balanced, valve 311 is open and valve 414 is closed, causing switch 415 to be OFF and the scaler boost function inactive.

Similarly to the system of FIG. 9, in the system of FIG. 10 de-activation of the 3-way control valve 103 depressurizes first actuator port 221 via open valve 311 faster than second port 222, resulting in the excess pressure at the second port that may temporarily overcome the spring bias and pushes piston rod 230 towards valve 414 and away from valve 311, closing valve 311 for the time interval $\Delta t_1$ when the excess pressure at port 222 relative to port 221 exceeds the first threshold $\Delta P_1$. When valve 311 is a 3-way valve, compressed air continues to escape from port 221 if 3-way control valve 103 remains disengaged.

If the control valve 103 is re-engaged sometime during the time interval while valve 311 is closed, compressed air from source 101 may re-pressurize port 222 to its full pressure, causing the excess pressure at port 222 relative to port 221 to exceed the second threshold $\Delta P_2$ that is sufficient to push piston rode 230 to a position where its second end 232 engages valve 414 as illustrated by dotted lines in the figure, permitting compressed air from fluid supply line 404 to actuate pneumatically-actuated electrical switch 415, thereby shorting boost terminal 371 to activate the scaler boost function. Disengaging control valve 103 for a time interval sufficiently exceeding $\Delta t_1$ causes actuator 250 to relax to its default state wherein spring 254 pushes piston 255 to the default position to keep valve 311 open and valve 414 closed.

Figure 11:
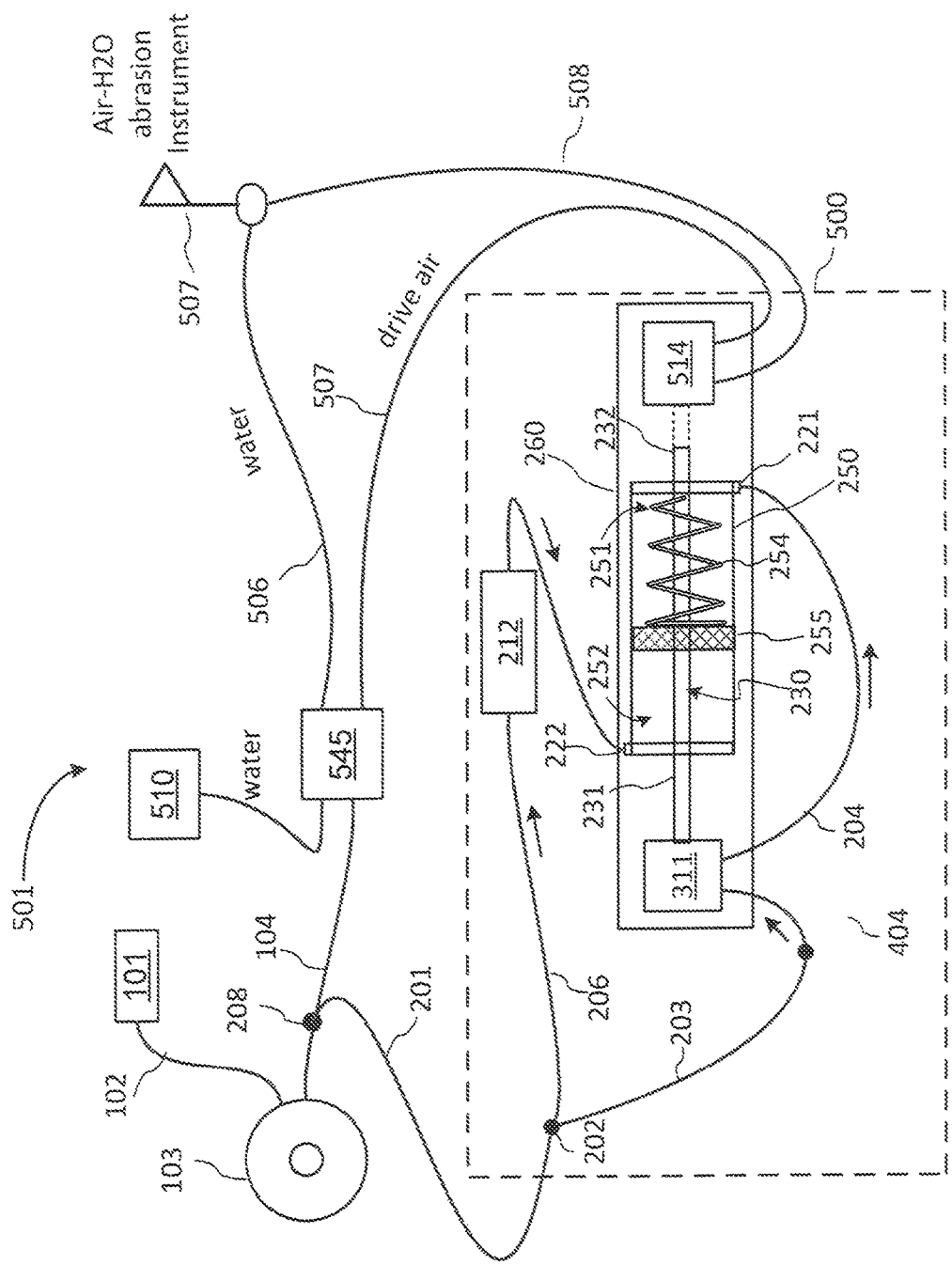
FIG. 11 is a schematic circuit diagram of a system wherein a bistable fluid-operated circuit with a spring-biased double-sided pneumatic cylinder actuator acts on a valve to shut down the supply of drive air to activate a rinse-only function for an Air-H2O abrasion instrument in response to a pressure signal.

Turning now to FIG. 11, in yet another embodiment an auxiliary bistable fluid-operated circuit 500 is used to temporary activate a rinse-only function by de-activating the provisioning of compressed air to an air H2O abrasion instrument or tool 507. Elements in FIG. 11 that are functionally same or substantially similar to corresponding elements in FIGS. 7-10 are labeled with the same reference numerals and may not be described again. A dental air abrasion system 501 may include a selector block 545 that provides water from water supply 510 to an air abrasion instrument or tool 507. Selector 545 may include one or more variable restrictors (not shown) to regulate tool 507 speed and/or the flow of water. The air abrasion instrument is activated when 3-way control valve 103 is engaged and provides compressed air to tool 507 via optional selector 545 and activation valve 514, which is normally open and may be a 3-way valve. Circuit 500 may be viewed as an embodiment of circuit 400 of FIG. 10, with actuator 250 which in its default state engages first port valve 311 to keep it open and, when actuated by excess pressure at port 222, disengages valve 311 to close it and engages valve 514 to close it. In the illustrated embodiment circuit 500 is structurally and functionally similar to circuit 400, except that normally open valve 514 replaces normally closed valve 414. In operation valve 514 receives compressed air from selector 545 via fluid supply line 507, and is open in the standby mode of circuit 500 wherein actuator 250 is in the default state, permitting the compressed air to enter tool 507 via fluid supply line 508. In another embodiment divider 28, where circuit 500 taps in for compressed air, may be disposed after selector 545, in the supply line 507.

Similarly to the system of FIG. 10, in the system of FIG. 11 deactivation of the 3-way control valve 103 depressurizes first actuator port 221 via open valve 311 faster than second port 222 is depressurized via FCM 212, resulting in the excess pressure at the second port that may temporarily overcome the spring bias and pushes piston 255 with rod 230 towards valve 514 and away from valve 311, closing valve 311 for the time interval $\Delta t_1$ when the excess pressure at port 222 relative to port 221 exceeds the first threshold $\Delta P_1$. When valve 311 is a 3-way valve, compressed air continues to escape from port 221 if 3-way control valve 103 remains disengaged. If 3-way control valve 103 is re-engaged sometime during the time interval while valve 311 is closed, compressed air from source 101 may re-pressurize port 222 to its full pressure, reinforcing the excess pressure at port 222 relative to port 221 to exceed the second threshold $\Delta P_2$ that is sufficient to push piston rode 230 to a position where its second end 232 engages valve 514 as illustrated by dotted lines in the figure, closing it and blocking compressed air from fluid supply line 507 from driving the air abrasion instrument 507, thereby activating the rinse-only mode of operation of tool 507. Disengaging control valve 103 for a time interval sufficiently exceeding the life time of the transitory circuit mode $\Delta t_1$ causes actuator 250 to relax to its default state wherein spring 254 pushes rod 230 to keep both valves 311 and 514 open, so that when control valve 103 is reactivated, compressed air again reaches the abrasion instrument 507 to drive it.

Figure 12:
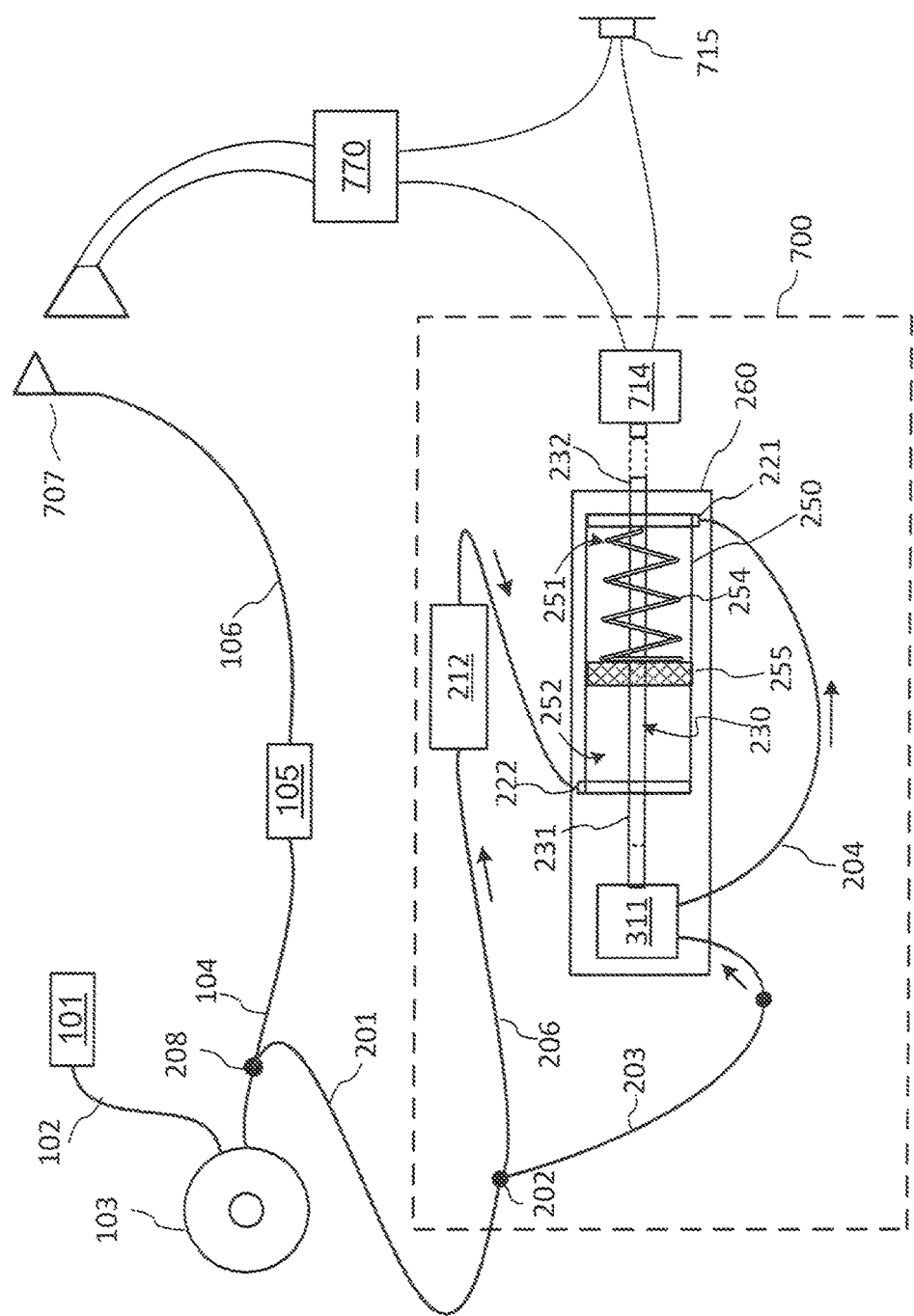
FIG. 12 is a schematic circuit diagram of a system wherein a bistable fluid-operated circuit with a spring-biased double-sided pneumatic cylinder actuator acts on a latching electrical switch to turn on electrical power to a dust collector.

Turning now to FIG. 12, there is illustrated a system wherein an embodiment of 700 of ancillary circuit 300 of FIG. 9 is used to temporary activate a dust collector 770 by turning on electrical switch 714 that turns on or off electrical power to the dust collector; the source of electrical power is indicated at 715 and may be, for example, a power outlet. Elements in FIG. 12 that are functionally same or substantially similar to corresponding elements in FIGS. 7-9 are labeled with the same reference numerals and may not be described again. Dental tool 707 is driven by compressed air, the supply of which is controlled by 3-way control valve 103, which may be foot-activated. Dental tool 707 may be, for example, an air driven Laboratory handpiece for adjusting ceramics or crown and bridge work. For some work an operator may want dust collector 770 on and waiting for when there is heavy cutting. For other work dust collector may not be needed to be turned on. Circuit 700 can activate dust collector 770 by actuating and turning on switch 714, which replaces switch 314 of FIG. 9 that activates the scaler boost function in the system of FIG. 9. In one embodiment switch 714 may be a latching push-button switch, which, once turned on by a brief de-activation of 3-way control valve 103 and a short-term drop in the fluid pressure at input supply line 201, remains switched on even after the system is subsequently depressurized by deactivating control valve 103 for a longer period of time. Switch 714 may be turned off again, and the dust collection function deactivated, by activating and then briefly deactivating control valve 103.

Although the embodiments illustrated in FIGS. 7-12 are described hereinabove with reference to air-driven tools and instruments used in dentistry, it will be appreciate that the same or similar circuits may be used in other, non-dental applications where pressure-driven tools and instruments are used.

Figure 13:
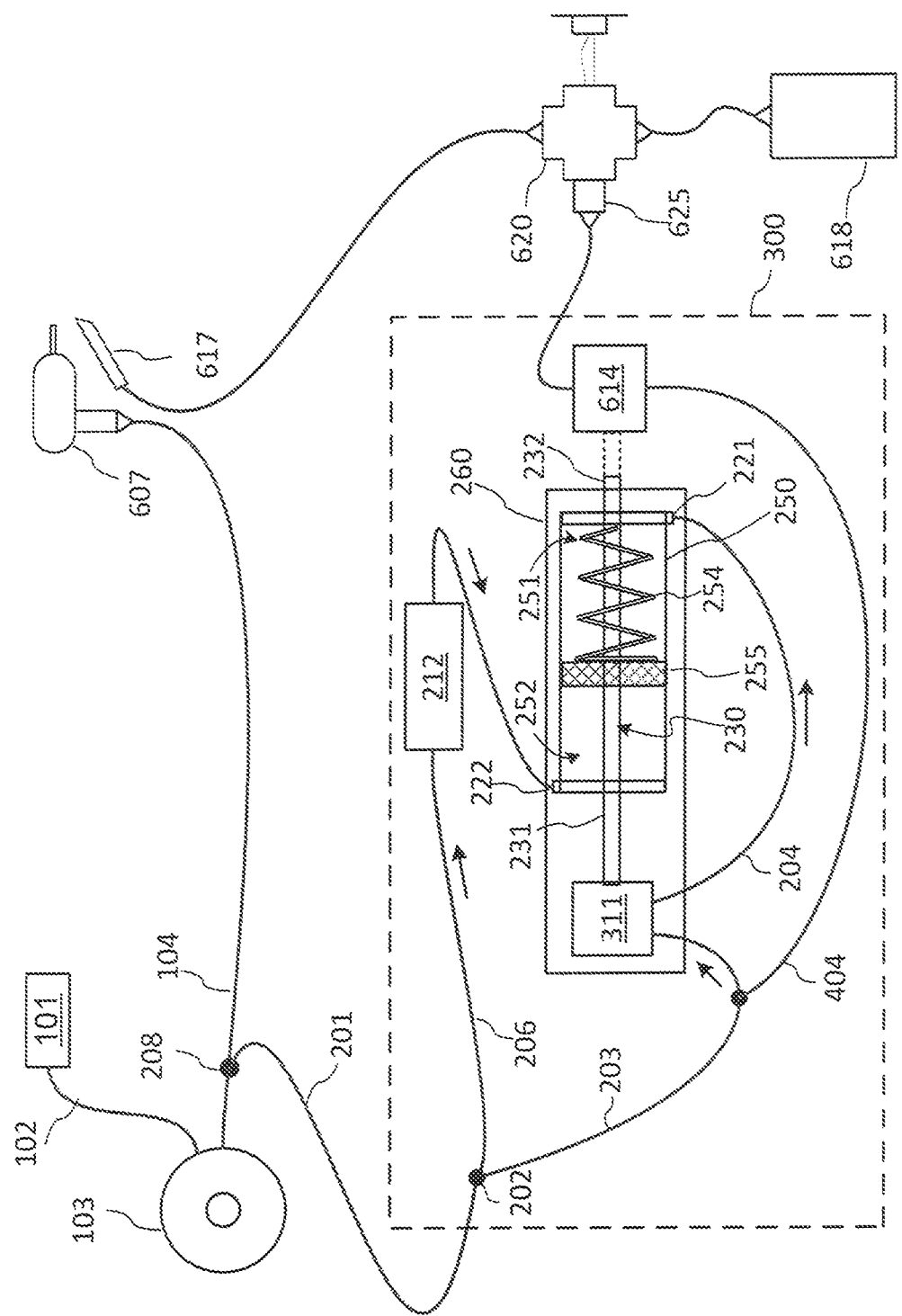
FIG. 13 is a schematic circuit diagram of a system wherein a bistable fluid-operated circuit with a spring-biased double-sided pneumatic cylinder actuator turns on or off the supply of cutting fluid to a fluid-operated metal cutting instrument.

Referring to FIG. 13, there is illustrated an example system wherein ancillary circuit 300 described hereinabove with reference to FIG. 9 is used to connect to air supply line 104 of a pneumatically driven metal cutting or machining instrument 607, such as a drill, to control the supply of cutting fluid, such as suitable liquid coolant, to the interface between a cutting edge of the tool and the material being cut using a coolant delivery element 617. Elements in FIG. 13 that are functionally same or similar to corresponding elements in FIG. 9 are labeled with same reference numerals and may not be described again. Valve 614, which may be a 3-way valve, regulates the delivery of compressed air to a pneumatically operated electrical switch 625 that, responsive to compressed air signal from valve 614, turns on or off an electrical pump 620. Electrical pump 620, when on, pumps liquid coolant to the coolant delivery element 617. In the standby mode of circuit 300 valve 614 is closed, switch 625 turned off, and no cutting fluid is supplied to fluid delivery element 617. When desired, the operator of drill 607 may briefly deactivate control valve 103, causing actuator 250 to switch to the activated state in which piston rod 230 engages valve 614 so as to open it, permitting compressed air from supply line 404 to act on pneumatic switch 625 so as to turn on pump 620, activating the delivery of liquid coolant to the tool. Deactivating control valve 103 for a longer time causes actuator 250 to relax to its default state and circuit 300 to return to the standby mode, wherein rod 230 keeps first port valve 311 open.

Example embodiments described hereinabove illustrated a method to activate an on-demand function in a circuit during normal operation thereof, including circuits having a main 3-way control valve that is configured to control the delivery of fluid under pressure to an instrument. The method may generally include tapping an output of the 3-way control valve to a fluid-operated bistable circuit (FOBC), such as circuits 130, 200, 300, 400, 500, 600, or 700 described hereinabove, which is configured to transition from a standby mode to an actuating mode by a drop of input fluid pressure lasting shorter than a first time interval, and to return to the standby mode if the drop in input pressure lasts longer than the first time interval. The method may further include coupling the FOBC to a function-activating valve or switch for actuation thereof when the FOBC is in the actuating mode, wherein the function-activating valve or switch is configured to activate the on-demand function.

The FOBC may include a fluid-operated biased actuator (FOBA), which in the example embodiments described above is exemplified by actuator 250, that has first and second actuator ports that are independently pressurizable by the fluid, and that is configured to be actuated in response to a pressure imbalance between the first and second actuator ports, the pressure imbalance defined by an excess fluid pressure at the second actuator port relative to the first actuator port. The FOBA may also be configured to return to a default state when the first and second actuator ports are pressure-balanced. Activating the on-demand function in the system during its normal operation may then include the following steps:

i) upon activation of the 3-way valve, permitting the fluid to pressurize the first actuator port through a first valve and to pressurize the second actuator ports through a flow control module, wherein in the standby mode the first valve is open permitting the first and second actuator ports to be pressurized in a balanced manner keeping the FOBA in the default state;

ii) upon de-activation of the 3-way valve causing the drop of the input fluid pressure, using the flow control module to restrict a back-flow of the fluid from the second actuator port to a greater degree than from the first actuator port, thereby effecting a temporary pressure imbalance between the first and second actuator ports;

iii) causing the FOBA to close the first valve when actuated by the temporary pressure imbalance between the first and second actuator ports, thereby at least temporary preventing the fluid from the 3-way valve to re-pressurize the first actuator port;

iv) upon re-activation of the 3-way valve within the first time interval $\Delta t_1$ while the first valve remains closed, causing the FOBC to operate in the actuating mode by permitting the fluid from the output of the 3-way valve to re-pressurize only the second actuator port thereby reinforcing the pressure imbalance between the first and second actuator port and re-actuating the FOBA; and, v) permitting the FOBA, when re-actuated by the reinforced pressure imbalance between the first and second actuator ports, to actuate the function-activating valve or switch for activating the on-demand function while keeping the first valve closed. A subsequent de-activation of the 3-way valve for duration of time longer than the first time interval may cause the FOBA to open the first valve thereby returning the FOBC to the standby mode.

It will be appreciated that the embodiments described hereinabove are by way of example only and numerous other embodiments may be envisioned by those skilled in the art having the benefit of the present disclosure.

For example, particular embodiments of the bistable pressure-operated apparatus and circuit of the present disclosure illustrated in FIGS. 9-13 have been described with reference to pneumatically driven instruments, with the term 'fluid' in the context of pneumatic instruments referring to air or other suitable gas, and the term "pressurized fluid" referring to compressed air. It will be appreciated however that circuits, elements and modules of the type described hereinabove with reference to FIGS. 7-12 may be easily adapted for systems and instruments operated by pressurized fluids other than compressed air or gas, including liquids, such as but not limited to water, that are supplied under pressure. Accordingly in such embodiments the two-port spring-biased cylinder 250 may be in the form of a hydraulic, rather than a pneumatic, cylinder that responds to an imbalance of fluid pressure at its ports, and which may in at least some embodiments return to a default state when the pressure is balanced.

Furthermore, valves and switches described hereinabove as coupled to the actuator cylinder may not require to be completely physically separated from the piston rod of the actuator when disengaged to be closed or open, and instead may remain mechanically coupled to the rod and be switched between their states by the force of axial motion of the piston rod in either direction. Thus, in the context of this specification the term 'disengaged', 'disengaging' and their variants may mean the movement of piston rod in a direction away from the valve or switch, without ever becoming fully detached therefrom. Fluid supply lines 201, 203, 206, 304, 404, serving as conduits for pressurized fluids in various embodiments described hereinabove may be in any suitable form that permits pressure-tight supply of pressurized fluids to respective tools, valves, dividers, ports, and other elements, such as but not exclusively in the form of flexible tubing or metal or plastic pipes.

Furthermore, although particular embodiments of the bistable pressure-operated apparatus and circuit of the present disclosure illustrated in FIGS. 9-13 utilize a double-ended double-action cylinder actuator with the first port valve (211, 311) and a function activation valve or switch (214, 314, 414, 514, 614, 714) disposed at opposing ends of the double-ended cylinder, other embodiments may utilize a single-ended pneumatic or hydraulic cylinder to actuate both the first port valve and the function activating valve or switch.

Figures 14, 15:
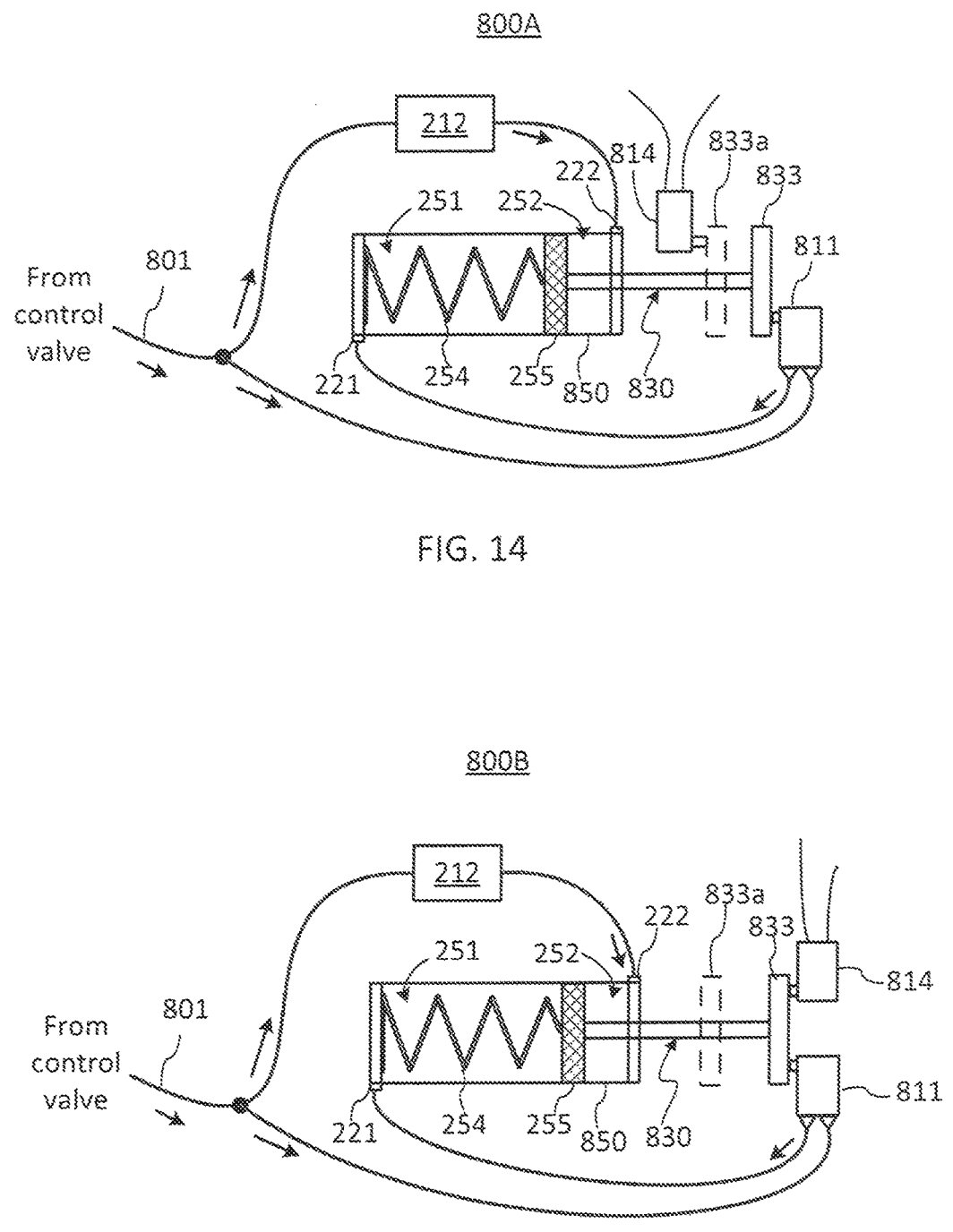

FIG. 14 illustrates one such example embodiment 800A of a dynamically-bistable fluid-operate apparatus, with a single-ended double-action cylinder 850 enclosing a pressure-movable piston 250 that separates the first and second chambers 252, 251 having first and second actuator port 221, 222. Input fluid line 801 connects to an output port of a control valve as described hereinabove. A piston rod 830 extends through one end of the cylinder, with an end portion 833 configured to engage a first port valve 833 in the default state or a function-activating valve or switch 814 in an actuated state, depending on the piston position and responsive to the pressure imbalance between the first and second actuator ports 221 and 222. The first port valve 811 and the function-activating valve or prism 814 may both be momentary valves, or a momentary valve and a momentary switch, which are normally closed, and open when engaged by the rod 830. FIG. 14 illustrates the default position, with the activated position, in which the end portion 833 of the rod 830 engages the function-activating valve or switch 814, shown with a dashed contour line indicated as 833a. It will be appreciated that the apparatus of FIG. 14 may be modified to use momentary valves, or a momentary valve and a momentary switch, which are normally open, by exchanging their positions along the cylinder' axis. Valve 814 and valve or switch 814 may be for example a mechanically-actuated push-button valve or a mechanically-actuated push-button switch.

FIG. 15 illustrates another embodiment 800B wherein the single-ended double-action cylinder 850 is used to simultaneously actuate the first port valve 811 and the function-activating valve or prism 814. Valve 811 may be normally closed and valve or switch 814 may be normally open. In the default state of the actuator the end portion 833 of the piston rod 830 engages both the first port valve 811 and the function-activating valve or prism 814, turning valve 811 open and valve or switch 814 closed. In the activated state the end portion 833 of the piston rod 830 is moved to a position indicated at 833a, disengaging from both the first port valve 811 and the function-activating valve or prism 814, letting valve 811 to close and valve or switch 814 to open. It will be appreciated that the apparatus of FIG. 15 may be modified to use a normally open valve for valve 811 and a normally closed valve or switch for valve or switch 811, by moving them to be engaged in the actuated state when the end portion 833 is in the default position 833a.

In embodiments wherein element 814 is a valve controlling the flow of pressurized fluid from a control valve to an instrument, the embodiment of FIG. 14 may be preferable over that of FIG. 15, as it may be configured so that valve or switch 814 remains closed until the control valve is re-activated, thereby allowing the full system pressure in the apparatus to be restored faster. It will be further appreciated that the illustrated shape of the end portion 833 is by way of example only.

Furthermore, some embodiments may utilize coupling means other than piston rod 230 to couple piston 255 to first port valve 211 or 311 and activation valve or switch 214, 314, 414, 514, or 714. For example, the respective valves and/or switches may be electrically activated rather than mechanically, and be electrically coupled to sensors that detect position of piston 255 within actuator 250, so as to change the state of the respective valve or switch depending on the piston position as described hereinabove with reference to specific embodiments. In some embodiments flow control module 212 may be mounted to port 222 eliminating the air supply line therebetween. In some less preferred embodiments flow control module 212 may be simply in the form of a flow restrictor.

Furthermore, although embodiments of the fluid-operated apparatus for activating and/or deactivating a function have been described hereinabove in the context of systems where the apparatus is a part of an auxiliary circuit connected in parallel to a primary fluid-supply circuit of a fluid-driven tool, and the function being activated or deactivated by the apparatus is auxiliary to a default operation of the primary circuit, it will be appreciated that the fluid-operated apparatus embodiments of which are described hereinabove can also be operated within a primary fluid-supply circuit of a fluid-driven device, instrument, or tool. For example, connecting the fluid-operated apparatus that in its standby mode requires an initial activation and then a brief deactivation of a control valve to turn on a tool or a function thereof, and which returns to a standby mode after a control valve deactivation for a longer time, may be useful to provide additional safety against an undesired activation of the tool when the control valve is activated by accident.

Numerous other modifications and variations will become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, features disclosed hereinabove with reference to a specific embodiment may be incorporated in other described embodiments or their variants. Of course, numerous other embodiments may be envisaged, without departing from the spirit and scope of the invention.

I claim:

1. An apparatus for activating an on-demand function, the apparatus comprising:
   a fluid-operated bistable circuit (FOBC) comprising one or more circuit ports configured to be pressurized by connecting to a source of fluid under pressure, wherein the FOBC is configured to:
      operate in a standby mode when the one or more circuit ports are pressurized by the fluid after being depressurized for at least a first time interval,
      switch to an actuating mode when the one or more circuit ports are briefly depressurized for a time interval shorter than the first time interval and then pressurized again, and
      return to the standby mode from the actuating mode if the one or more circuit ports remain depressurized for a time interval longer than the first time interval, and;
   wherein the FOBC is further configured to actuate a function-activating valve or switch when in the actuating mode, wherein the function-activating valve or switch is operational to activate the on-demand function.

2. The apparatus of claim 1,
   wherein the one or more circuit ports comprise a first valve and a flow control module, wherein the first valve is open in the standby mode and closed in the actuating mode;
   wherein the FOBC includes a fluid-operated biased actuator (FOBA) comprising a first actuator port and a second actuator port, said first and second actuator ports being independently pressurizable by the fluid received from the first valve and from the flow control module, respectively, wherein the FOBA is configured to be actuated by a pressure imbalance between the first and second actuator ports;
   wherein the FOBA is operatively coupled to the function-activating switch or valve for actuating thereof in response to an excess fluid pressure at the second actuator port relative to the first actuator port that exceeds a first threshold; and,
   wherein the FOBA is operatively coupled to the first valve for closing thereof in response to the excess fluid pressure at the second actuator port that exceeds a second threshold that is equal or smaller than the first threshold, wherein the first threshold is equal or smaller than the excess fluid pressure at the second actuator port when the one or more circuit ports are all pressurized and the first valve is closed.

3. The apparatus of claim 2 wherein the flow control module is configured to throttle a back flow of the fluid from the second actuator port when the one or more circuit ports are depressurized so as to cause the second actuator port to depressurize more slowly than the first actuator port and to at least temporary cause the excess fluid pressure at the second actuator port to exceed the second threshold, thereby actuating the FOBA to close the first valve.

4. The apparatus of claim 3 wherein the FOBA is configured to open the first valve when the first and second actuator ports are both substantially equally pressurized or both substantially equally depressurized.

5. The apparatus of claim 3 wherein the FOBA comprises:
   a double-acting cylinder enclosing a piston movably disposed therewithin so as to define first and second pressure-tight chambers separated by the piston, wherein the first actuator port provides a conduit for the fluid to flow in and out of the first chamber and the second actuator port provides a conduit for the fluid to flow in and out of the second chamber, wherein the piston is movable by the excess fluid pressure at the second actuator port;
   a spring member disposed to bias the piston to a default position when the first and second actuator ports are pressure-balanced;
   an actuator coupling configured to communicate movement of the piston to the first valve so as to cause the first valve to be open if the piston is in the default position, and to cause the first valve to be closed when the piston is moved out of the default position by the excess fluid pressure exceeding the second threshold.

6. The apparatus of claim 5 wherein the actuator coupling is configured to communicate movement of the piston to the function-activating valve or switch to activate the function when the piston is moved out of the default position by the excess fluid pressure at the second actuator port that exceeds the first threshold.

7. The apparatus of claim 6 wherein the actuator coupling comprises a piston rod fixedly attached to the piston and comprising one or more end portions extending out of the cylinder, the piston rod axially movable with the piston by the excess fluid pressure at the second actuator port with the one more end portions configured for engaging the first valve and/or the function-activating valve or switch responsive to the excess fluid pressure at the second actuator port.

8. The apparatus of claim 7 wherein the first valve is normally open and is disposed to be closed by the piston rod when the piston is moved out of the default position by the excess pressure at the second port exceeding the second threshold.

9. The apparatus of claim 7 wherein the on-demand function relates to an operation of a circuit comprising a three-way control valve configured to control the delivery of fluid under pressure to a fluid operated instrument during normal operation thereof, the apparatus further comprising:
   one or more supply lines for connecting the first valve and the flow control module to an output of the 3-way control valve to provide the fluid under pressure to the first and second actuator ports when the control valve is activated by an operator, the 3-way control valve permitting one or more supply lines to be depressurized when deactivated; and,
   the function-activating valve or switch disposed to be actuated by the FOBA responsive to a brief deactivation of the 3-way control valve followed by a re-activation thereof during normal operation of the instrument, said brief deactivation causing the first valve to close and said re-activation causing the excess fluid pressure at the second actuator port sufficient for actuating the function-activating valve or switch.

10. The apparatus of claim 9 wherein the function-activating valve or switch comprises a second valve disposed to control flow of the fluid from the 3-way control valve to the instrument, the second valve further disposed to be actuated by the FOBA to be open or closed in dependence on the excess pressure at the second actuator port.

11. The apparatus of claim 10 wherein each of the first and second valves are normally closed, and wherein the flow control module is configured to throttle the backflow of the fluid from the second actuator ports so that, when the 3-way control valve is deactivated thereby permitting the one or more supply lines to depressurize, the excess pressure at the second actuator port remains below the first threshold so that the second valve remains closed until the 3-way control valve is re-activated.

12. The apparatus of claim 9 wherein the function-activating valve or switch comprises an electrical switch configured to activate or de-activate the on-demand function and disposed to be actuated by the FOBA to be switched on or off in dependence on the excess pressure at the second actuator port.

13. The apparatus of claim 6 wherein the actuator coupling comprises a piston rod fixedly attached to the piston and comprising one or more end portions extending out of the cylinder, the piston rod axially movable with the piston by the excess fluid pressure at the second actuator port with the one more end portions engaging either one of: the first valve, or the function activating valve or switch responsive to the excess fluid pressure at the second actuator port.

14. The apparatus of claim 13 wherein the first valve is normally closed and is disposed to be open by the piston rod when the piston is in the default position.

15. An apparatus for activating an on-demand function in a circuit comprising a three-way control valve configured to control the delivery of fluid under pressure, the apparatus comprising:
   a fluid-operated biased actuator (FOBA) comprising a first actuator port and a second actuator port, said first and second actuator ports being independently pressurizable by the fluid, the FOBA configured to be responsive to an excess fluid pressure at the second actuator port relative to a balanced relationships with the first actuator port;
   a first fluid supply line for connecting the first actuator port to the output of the 3-way control valve, the first fluid supply line comprising a first valve that is operatively coupled to the FOBA;
   a second fluid supply line for connecting the second actuator port to the output of the 3-way control valve, the second fluid supply line comprising a flow control module;
   wherein the first valve, when open, permits the fluid from the three-way control valve to pressurize the first actuator port when the first three-way control valve is activated, and, when closed, blocks or at least restricts the fluid from pressurizing the first actuator port;
   wherein the FOBA is configured to actuate a function-activating valve or switch for activating the function when the excess fluid pressure at the second actuator port exceeds a first threshold;
   wherein the FOBA is further configured to control the first valve responsive to the excess pressure at the second actuator port, so as to keep the first valve open when the first and second actuator ports are pressure-balanced, and to close the first valve when the excess fluid pressure at the second actuator port exceeds a second threshold that is equal or smaller than the first threshold;
   wherein the flow control module is configured to throttle a back-flow of the fluid from the second actuator port, so as to cause the second actuator port to depressurize more slowly than the first actuator port when the three-way control valve is disengaged by the operator, thereby causing the FOBA to at least temporary close the first valve for a first time interval and to open the first valve after the first time interval is expired if the three-way valve remains disengaged; and,
   wherein the FOBA actuates the function-activating valve or switch if the control three-way valve is re-engaged while the first valve remains closed.

16. A method to activate an on-demand function in a circuit during normal operation thereof, the circuit comprising a 3-way control valve configured to control the delivery of fluid under pressure to an instrument, the method comprising:
   tapping an output of the 3-way control valve to a fluid-operated bistable circuit (FOBC) configured to transition from a standby mode to an actuating mode by a drop of input fluid pressure lasting shorter than a first time interval, and to return to the standby mode if the drop lasts longer than the first time interval, and;
   coupling the FOBC to a function-activating valve or switch for actuation thereof when the FOBC is in the actuating mode, wherein the function-activating valve or switch is configured to activate the on-demand function.

17. The method of claim 16 wherein the FOBC includes a fluid-operated biased actuator (FOBA) comprising a first actuator port and a second actuator port, said first and second actuator ports being independently pressurizable by the fluid, wherein the FOBA is configured to be actuated in response to a pressure imbalance between the first and second actuator ports, the pressure imbalance defined by an excess fluid pressure at the second actuator port relative to the first actuator port, and to return to a default state when the first and second actuator ports are pressure-balanced, the method comprising:
   upon activation of the 3-way valve, permitting the fluid to pressurize the first actuator port through a first valve and to pressurize the second actuator ports through a flow control module, wherein in the standby mode the first valve is open permitting the first and second actuator ports to be pressurized in a balanced manner keeping the FOBA in the default state;
   upon de-activation of the 3-way valve causing the drop of the input fluid pressure, using the flow control module to restrict a back-flow of the fluid from the second actuator port to a greater degree than from the first actuator port, thereby effecting a temporary pressure imbalance between the first and second actuator ports;
   causing the FOBA to close the first valve when actuated by the temporary pressure imbalance between the first and second actuator ports, thereby at least temporary preventing the fluid from the 3-way valve to re-pressurize the first actuator port;
   upon re-activation of the 3-way valve within a first time interval while the first valve remains closed, causing the FOBC to operate in the actuating mode by permitting the fluid from the output of the 3-way valve to re-pressurize only the second actuator port thereby reinforcing the pressure imbalance between the first and second actuator port and re-actuating the FOBA; and,
   permitting the FOBA, when re-actuated by the reinforced pressure imbalance between the first and second actuator ports, to actuate the function-activating valve or switch for activating the on-demand function while keeping the first valve closed.

18. The method of claim 17 wherein a subsequent de-activation of the 3-way valve for duration of time longer than the first time interval causes the FOBA to open the first valve thereby returning the FOBC to the standby mode.

* * * * *